(12) United States Patent
Beardsley et al.

(10) Patent No.: US 10,024,716 B2
(45) Date of Patent: *Jul. 17, 2018

(54) FIELD LENS CORRECTED THREE MIRROR ANASTIGMAT SPECTROGRAPH

(71) Applicants: Burt J. Beardsley, Tucson, AZ (US); Wendy Beardsley, Tucson, AZ (US)

(72) Inventors: Burt J. Beardsley, Tucson, AZ (US); Wendy Beardsley, Tucson, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/614,307

(22) Filed: Jun. 5, 2017

(65) Prior Publication Data

US 2017/0268927 A1    Sep. 21, 2017

Related U.S. Application Data

(63) Continuation-in-part of application No. 15/335,315, filed on Oct. 26, 2016, now Pat. No. 9,677,932.

(Continued)

(51) Int. Cl.
| | |
|---|---|
| *G01J 3/28* | (2006.01) |
| *G01J 3/02* | (2006.01) |
| *G02B 17/08* | (2006.01) |
| *G02B 5/00* | (2006.01) |
| *G02B 27/30* | (2006.01) |
| *G02B 5/04* | (2006.01) |
| *G02B 5/18* | (2006.01) |
| *G01N 21/71* | (2006.01) |
| *G01J 3/18* | (2006.01) |
| *G01J 3/12* | (2006.01) |

(52) U.S. Cl.
CPC ............. *G01J 3/0208* (2013.01); *G01J 3/021* (2013.01); *G01J 3/0218* (2013.01); *G01J 3/1809* (2013.01); *G01J 3/2823* (2013.01); *G01N 21/718* (2013.01); *G02B 5/005* (2013.01); *G02B 5/04* (2013.01); *G02B 5/1842* (2013.01); *G02B 17/0832* (2013.01); *G02B 17/0848* (2013.01); *G02B 27/30* (2013.01); *G01J 2003/1208* (2013.01)

(58) Field of Classification Search
CPC ........ G01J 3/28; G01J 3/26; G01J 3/02; G01J 3/10; G01J 3/18
See application file for complete search history.

(56) References Cited

U.S. PATENT DOCUMENTS

| 9,677,932 B2 * | 6/2017 | Beardsley | ............... G01J 3/021 |
|---|---|---|---|
| 2009/0091753 A1 | 4/2009 | Beardsley | |

* cited by examiner

*Primary Examiner* — Abdullahi Nur
(74) *Attorney, Agent, or Firm* — Jiarong L. Lamiquiz; Quarles & Brady LLP

(57) ABSTRACT

A spectrograph that includes camera focusing optics with a primary mirror having a concave-shaped reflective mirror surface, a secondary mirror having a convex-shaped reflective mirror surface and positioned to receive light reflected by the primary mirror, a tertiary mirror having a concave reflective mirror surface and positioned to receive light reflected by the secondary mirror, and a field correcting lens comprising a convex lens surface in combination with a concave lens surface, wherein light received by said field correcting lens from said tertiary mirror enters said convex lens surface, traverses said field correcting lens, and exits from said concave lens surface. The optional field correcting lens is positioned such that the primary mirror, secondary mirror, tertiary mirror, and the field correcting lens share the common parent vertex axis.

27 Claims, 19 Drawing Sheets

Related U.S. Application Data

(60) Provisional application No. 62/246,398, filed on Oct. 26, 2015.

FIELD LENS CORRECTED THREE MIRROR ANASTIGMAT SPECTROGRAPH

CROSS-REFERENCE TO RELATED APPLICATIONS

This non-Provisional application is a Continuation-in-Part of a U.S. application having Ser. No. 15/335,315, filed on Oct. 26, 2016, which claims priority from a U.S. Provisional Application filed on Oct. 26, 2015 and having Ser. No. 62/246,398. The disclosure of each of the above-identified applications is incorporated herein by reference in its entirety.

TECHNOLOGY FIELD

This invention relates to optical instruments for use in the measurement of properties of light, and specifically to spectrographs including echelle, linear array, and imaging spectrographs.

BACKGROUND

An echelle spectrograph is an optical instrument that uses an echelle grating to diffract light with high dispersion and utilizes higher diffraction orders. As with other blazed diffraction gratings, the echelle grating contains a number of grooves. However, echelle gratings are specifically characterized by the large spacing between the grooves and, therefore, are characterized with a lower groove density than standard blazed gratings that are designed to be used in the $1^{st}$ diffraction order.

Light incident upon any ruled grating is split into several different diffraction orders. Each order is comprised of a different wavelength range that overlaps onto the same spatial location as light that is diffracted into other orders. The dispersion associated with each order is also different. The overlapping ranges of orders diffracted from the grating make it difficult to associate a particular wavelength with a given spatial location in the diffracted light. This ambiguity complicates the output spectrum and makes it more difficult to determine the correct wavelength emission produced by the source.

Although this overlap between diffraction orders is generally an unwanted side effect, echelle gratings specifically use this effect to enhance the performance of the spectrograph. To this end, a second cross-dispersing element is used to spatially separate the orders. The individual diffraction orders, each with a separate (and sometimes overlapping) wavelength range and resolution, can then be analyzed without ambiguity.

A lens-based spectrograph can have good resolution and very high throughput (~f/2) over a limited wavelength range. If the wavelength range of operation needs to be shifted from the design wavelength of the lenses, or if a broad wavelength range is required to be simultaneously acquired such as with an echelle spectrograph, then chromatic aberration limits spectral resolution of a lens-based instrument.

Typical broadband, all-reflective echelle spectrographs have a relatively high f/number, generally f/7 or greater camera focusing optics, limiting the total light that reaches the image plane and thereby decreasing the resulting image quality. Further, the high f/number of a typical echelle grating-based spectrograph prevents the use of such an instrument in certain applications such as Raman spectroscopy, where the detection of weak levels of light emission necessitates the use of a spectrograph with a very low f/number.

A linear array spectrograph uses a standard ruled grating, usually (but not always) in the $1^{st}$ order. A 1-D linear array sensor is combined with the spectrograph to make a very compact and inexpensive spectrometer. These instruments have limited wavelength coverage but can be appropriate for some applications such as Raman spectroscopy where a limited wavelength range is possible. All-reflective, linear array spectrographs usually implement camera focusing optics that are f/4 or slower, plus the linear array length and resolution can be limited by the quality of the camera focusing optics.

An imaging spectrograph is similar to a linear array spectrograph except that it utilizes a 2-D sensor. A tall entrance aperture can be used with an imaging spectrograph because the image plane is better corrected than a linear array spectrograph in the direction perpendicular to the grating dispersion. The tall entrance aperture permits either much better throughput or multiple fiber inputs aligned along the entrance aperture. The multiple fiber inputs can direct light from various light sources enabling simultaneous monitoring of multiple input channels. The tall slit allows the spectrograph to monitor wavelength information along one axis, while simultaneously measuring spatial information along the other axis. All-reflective imaging spectrographs are typically f/4 or slower, plus the size of the 2-D image plane is limited.

SUMMARY

Certain embodiments of the current disclosure include a primary mirror having a concave-shaped reflective mirror surface, a secondary mirror having a convex-shaped reflective mirror surface and positioned to receive light reflected by the primary mirror, a tertiary mirror having a spheroidal (spherical concave) reflective mirror surface and positioned to receive light reflected by the secondary mirror, and a field correcting lens comprising a first lens surface in combination with a second lens surface (positive meniscus lens), wherein light received by said field correcting lens from said tertiary mirror enters said convex lens surface, traverses said field correcting lens, and exits from said concave lens surface. The field correcting lens is positioned such that the primary mirror, secondary mirror, tertiary mirror, and the field correcting lens substantially share the common parent vertex axis.

Further, in certain embodiments, a spectrograph contains a diffraction grating; a primary mirror having a concave reflective surface and positioned to reflect light that has interacted with the diffraction grating; a secondary mirror having a convex reflective surface and positioned to receive said light from the primary mirror; a tertiary mirror having a concave reflective surface and positioned to receive said light reflected by the secondary mirror, wherein the primary mirror, the secondary mirror, and the tertiary mirror form a three-mirror anastigmat (TMA) with a shared TMA parent vertex axis; an entrance aperture; an aperture stop; and a collimator mirror positioned to receive light that has been transmitted through the entrance aperture and form a collimated beam of light directed towards the diffraction grating through the aperture stop.

Moreover, the diffraction grating is positioned to receive and diffract light that has passed through the aperture stop into a plurality of beams spatially dispersed by wavelength; the diffraction grating is configured to be rotatable about a first axis that is perpendicular to the surface of a first plane of the grating such that a dispersion direction is caused to be perpendicular to a second plane, the second plane passing through the primary mirror, the secondary mirror, and the tertiary mirror of the TMA; the diffraction grating configured to be rotatable about a second axis such that a rotation angle is substantially close to a blaze angle of the grating, wherein the second axis is parallel to a groove direction on the surface of the diffraction grating; and the diffraction grating configured to be rotatable in the first plane of the grating about a third axis at an angle chosen to result in cancellation of the geometric distortion and causing said plurality of beams to intersect an image plane along a straight line in the center of the image plane, wherein the third axis is perpendicular to the groove.

In addition, in certain embodiments, the diffraction grating is positioned to receive and diffract light that has passed through the aperture stop into a plurality of beams spatially dispersed by wavelength; the diffraction grating is configured to be rotatable about a first axis that is perpendicular to the surface of a first plane of the grating such that a dispersion direction is caused to be parallel to a second plane, the second plane passing through the primary mirror, the secondary mirror, and the tertiary mirror of the TMA; the diffraction grating configured to be rotatable about a second axis such that a rotation angle is substantially close to a blaze angle of the grating, wherein the second axis is parallel to a groove direction on the surface of the diffraction grating.

BRIEF DESCRIPTION OF THE DRAWINGS

The disclosure will be better understood from a reading of the following detailed description taken in conjunction with the drawings in which like reference designators are used to designate like elements, and in which.

DETAILED DESCRIPTION

This disclosure is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment.

The described features, structures, or characteristics of the disclosure may be combined in any suitable manner in one or more embodiments. In the following description, numerous specific details are recited to provide a thorough understanding of the embodiments of the disclosure. One skilled in the relevant art will recognize, however, that the disclosure may be practiced without one or more of the specific details, or with other methods, components, materials, and so forth. In other instances, well-known structures, materials, or operations are not shown or described in detail to avoid obscuring aspects of the disclosure.

Figure 1:
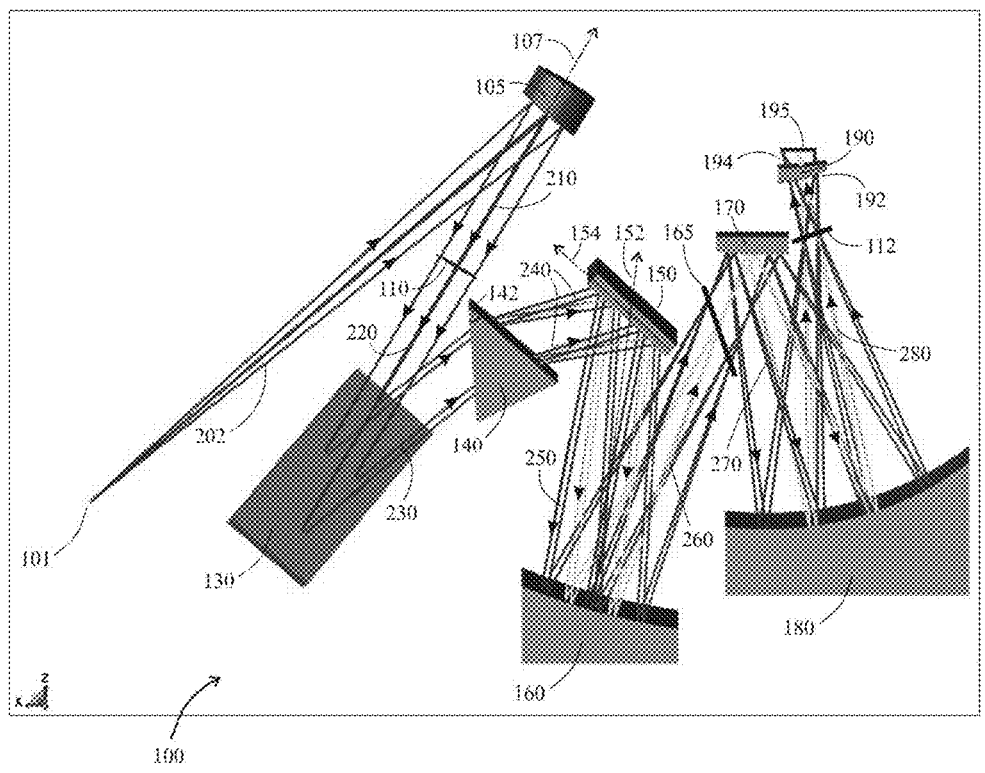
FIG. 1 illustrates the movement of radiation through one embodiment of the echelle spectrograph.
Figure 2:
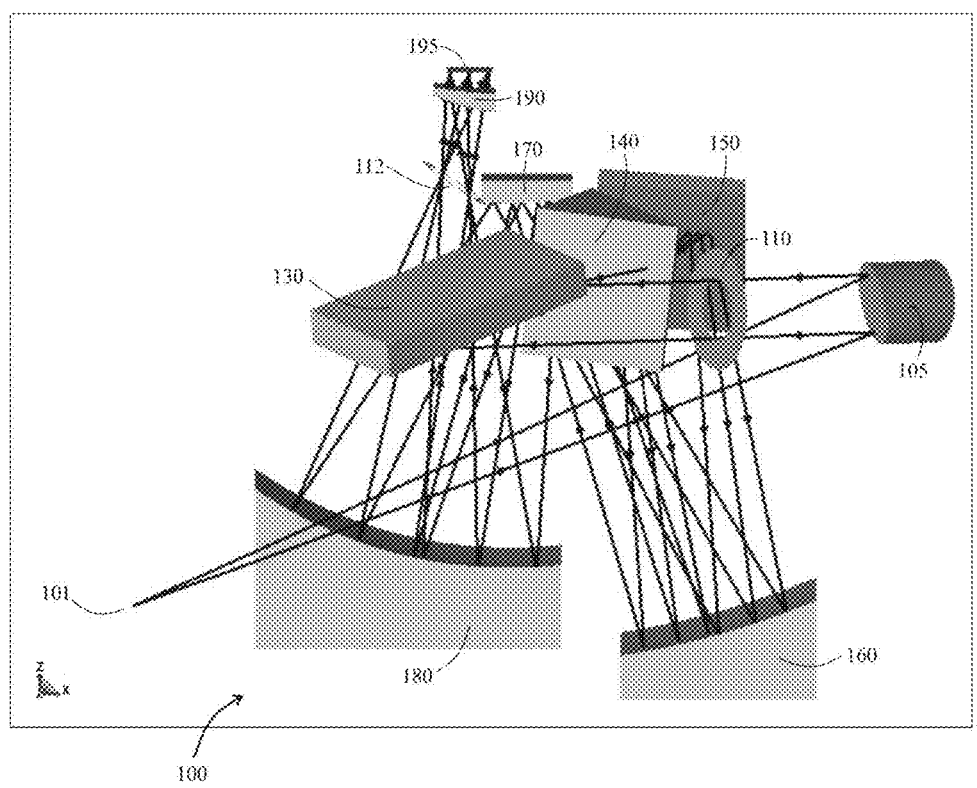
FIG. 2 shows a different embodiment of the echelle spectrograph.
Figure 3:
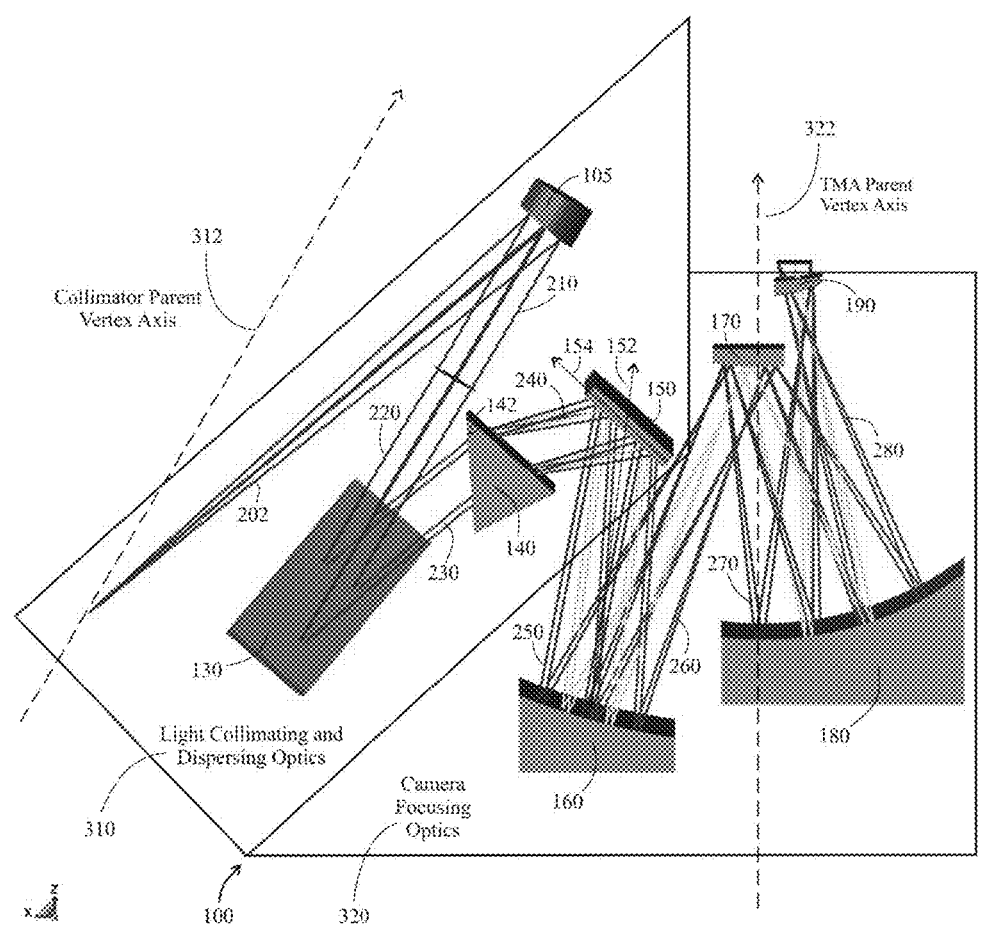
FIG. 3 demonstrates two components of the embodiment of the echelle spectrograph illustrated in FIG. 1.

Referring to FIG. 3, in certain embodiments, an echelle spectrograph 100 can be divided into two sets of components. The first set of components is light collimating and dispersing optics 310, and the second set of components is camera focusing optics 320. Referring to FIGS. 1 and 2, the first set 310 includes an entrance aperture 101, a collimator mirror 105, an aperture stop 110, a diffraction grating 130, a cross-dispersing prism 140, and a fold mirror 150. In certain embodiments, the fold mirror 150 comprises a reflector with a flat surface. Moreover, the fold mirror 150 has a first axis 152 that is defined in the plane of the mirror 150 (and, in reference to FIG. 1, substantially perpendicular to the plane of FIG. 1) and a second axis 154 that is contained in the same plane of the mirror 150 perpendicular to the first axis 152.

Further, the camera focusing optics 320 (FIG. 3) contains the optics configured to focus light onto the image plane, commonly referred to as the "camera focusing optics". This camera focusing optics 320 includes a combination of three mirrors aggregately configured as a three mirror anastigmat (TMA). Specifically, and referring again to FIG. 1, the TMA within the camera focusing optics 320 includes a primary mirror 160 having concave-shaped reflecting surface, a secondary mirror 170 having convex-shaped reflecting surface, and a tertiary mirror 180 having concave-shaped reflecting surface. The TMA is optically followed by a field correcting lens 190, which relates light incident thereon on an image plane 195. In some embodiments, the field correcting lens 190 is a positive meniscus field correcting lens. Further, the field correcting lens 190 is formed from an off-axis portion of a positive meniscus lens. In other embodiments, the field correcting lens 190 is a biconvex, piano-convex, piano-concave, or negative meniscus lens. In yet other embodiments, the field correcting lens 190 is a bi-concave corrective element. With different types of the field correcting lens used, the parent axis of the field corrective lens is located on or substantially close to the TMA parent vertex axis 322 shown in FIG. 3. "Substantially close" is defined as the vertex axis of the field corrective lens is translated in X or Y by less than a millimeter from the TMA parent vertex axis 322 or the parent vertex axis of the field corrective lens is tilted less than 1 degree with respect to the TMA parent vertex axis 322. The field correcting lens 190 is located between the tertiary mirror 180 and the image plane 195.

Figure 4:
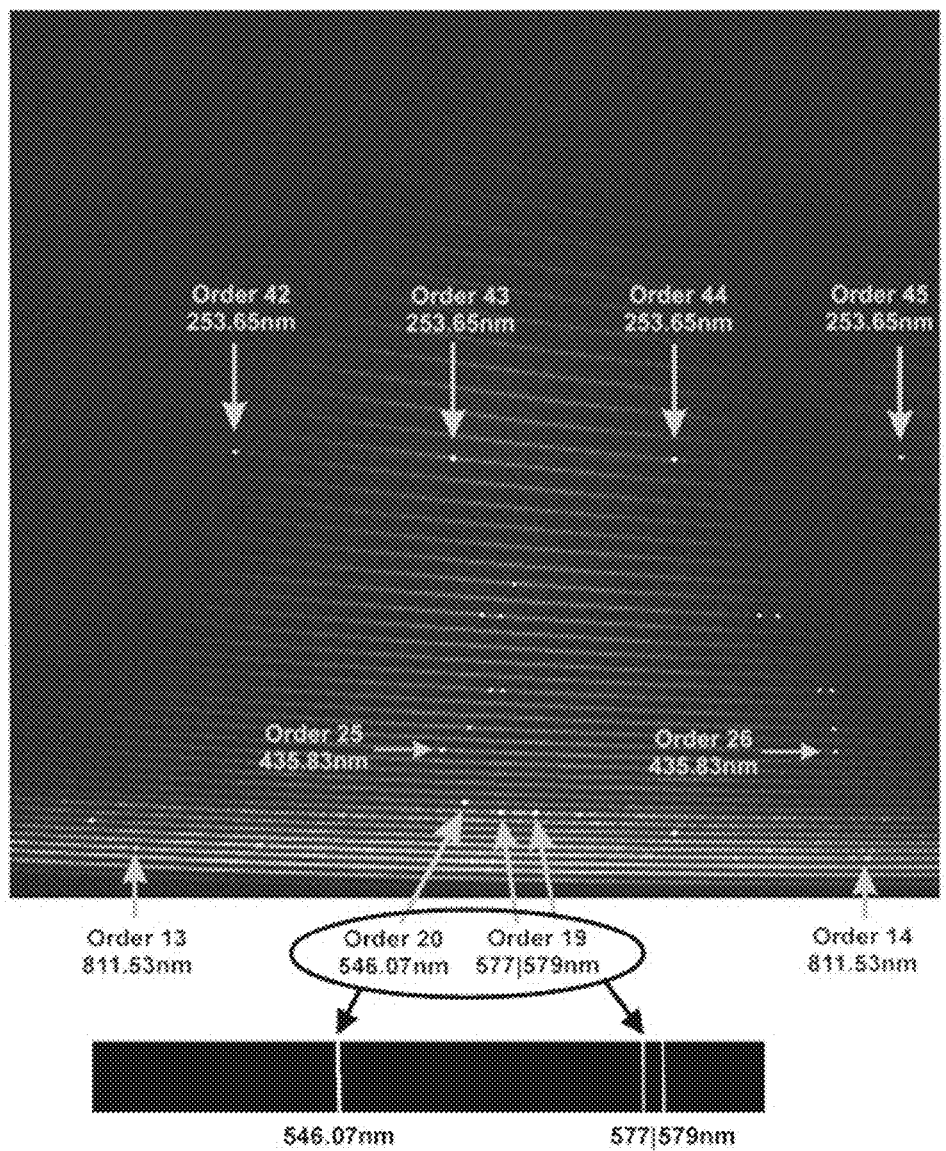
FIG. 4 demonstrates the echelle spectrograph's wavelength coverage and resolution (top image) and a standard Czerny-Turner imaging spectrograph's wavelength coverage and resolution (bottom image)

Referring to FIG. 1, light incident onto the fold mirror 150 is directed by the fold mirror 150 to first strike the primary mirror 160, and is further reflected to the secondary mirror 170. The mirror 170, in turn, redirects this light to the tertiary mirror 180. The TMA, with three off-axis mirrors, provides a much better corrected angular field of view than other types of camera focusing optics that utilize only one or two corrective surfaces. The more corrective surfaces an optical design has available, the smaller the optical aberrations can become and the larger the useable field of view. As an example, FIG. 4 shows comparison images from a standard Czerny-Turner (CT) type of spectrograph (bottom image) with an existing TMA-based EMU-120/65 spectrograph (EMU) from Catalina Scientific Instruments, LLC (top image). The EMU has three corrective surfaces in the camera focusing optics while the CT design has a single corrective element. The TMA-based EMU provides a highly corrected 2D image plane allowing multiple spectral orders to be displayed simultaneously on the image plane, resulting in excellent spectral resolution and very broad wavelength coverage. The CT design is limited to a very narrow wavelength band and can only operate in one diffraction order, typically $1^{st}$ order.

Referring to FIG. 1 again, in certain embodiments, a cone of light is accepted by the echelle spectrograph 100 through the entrance aperture 101 and then propagated toward the collimator mirror 105 as a cone of light 202. In the embodiments illustrated in FIGS. 1 and 2, the off-axis section of the collimator mirror 105 has a conic constant of −1 (rendering this off-axis section to be a parabolic section of the reflector 105) and radius of curvature of 1200 mm (rendering this off-axis section to be a concave portion of the reflector).

In further reference to FIGS. 1 and 2, light beam 202 is reflected by the collimator mirror 105 to produce a collimated beam of light 210. The beam 210 passes through the aperture stop 110, which is centered (107) on the bundle of rays arriving to the stop 110 from the collimator mirror 105. If the entrance aperture 101 is located at the focal point of the collimator parent vertex axis 312, the optical aberrations present in a wave front of the beam 210 are minimized or substantially absent, and therefore, the beam 210 approximates the perfectly collimated beam of light. In some embodiments, the entrance aperture 101 may be offset from the parent collimator mirror by less than 1 mm. Astigmatism introduced into the spectrograph by offsetting the entrance aperture can be used to cancel residual astigmatism found in the camera focusing optics 320 in FIG. 3.

As those skilled in the art readily appreciate, an aperture stop limits the brightness of an image by restricting the size of the angular cone of light passing through the entrance aperture and collimator mirror. Therefore, the aperture stop 110 is one of the primary components of an embodiment of the present system that controls the amount of light transmitted through echelle spectrograph 100. In certain embodiments, the aperture stop size can be user interchangeable to allow the desired amount of light into echelle spectrograph 100. Neglecting the effects of diffraction, a smaller aperture stop usually produces a sharper image at the image plane 195 as a result of reducing optical aberrations. Echelle spectrograph 100 can be optimized for maximum light throughput with a large aperture stop 110 or best spectral resolution with a small aperture stop 110. In the embodiment in FIG. 1, the aperture stop has been located half way between the collimator mirror and grating. Aperture stop 110 can also be located near the grating or anywhere between the collimator and diffraction grating as long as it does not block rays 202 going to collimator 105 or rays 230 traveling from grating 130 to prism 140.

Light beam 210 passes through the aperture stop 110, and forms the beam of light 220. Beam 220 is further directed onto the diffraction grating 130. The beam of light 220 carries polychromatic light that is electromagnetic radiation at a plurality of wavelengths. The nature of the light source determines the specific constituent wavelengths of light 220.

As those skilled in the art will readily appreciate, the echelle grating 130 spatially separates incident light beam 220 into a plurality of beams at respectively corresponding constituent wavelengths, i.e., light 220 is dispersed by echelle grating 130. When light beam 220 is incident on echelle grating 130 at an angle $\theta_i$ (measured from the normal to the surface of the grating), the incident light is diffracted into several beams. The beam that corresponds to direct transmission (or specular reflection in the case of a reflection grating) forms the zeroth order of diffraction, and is denoted with an index m=0. The other diffraction orders correspond to diffraction angles that are different from the specula angle of reflection and are represented by non-zero integer values of the index m. For a groove (grating) period d and an incident wavelength λ, the grating equation (1) gives the value of the diffracted angle $\theta_m(\lambda)$ in the order m:

$$d \times (\sin \theta_m(\lambda) + \sin \theta_i) = m \times \lambda \qquad (1)$$

In a related embodiment, the echelle grating 130 can be replaced with another grating of different groove density or blaze angle. Changing the blaze angle or groove period of grating 130 results in different spectral characteristics of light at the image plane 195, which in turn affects spectral resolution and diffraction order spacing. In different implementations, different echelle gratings 130 with different groove periods and/or blaze angles can be used.

Light 230 that is reflected by and/or diffracted at the diffraction grating 130 forms a plurality of beams dispersed according to the wavelength of light. The diffracted beams corresponding to consecutive diffraction orders spatially overlap, thereby making it difficult to determine the correct wavelength for a chosen spectral feature.

Light 230 is further directed onto a cross-dispersive prism 140, where it is further dispersed upon traversal of the prism 140 according to wavelength, but in a direction perpendicular to the dispersion direction of the grating.

Prism 140 controls the total range of wavelengths passing through to the image plane 195. By either changing the apex angle 142 of prism 140 or by changing the material of prism 140, different wavelength ranges can be utilized at the image plane 195. For example, in one embodiment of the echelle spectrograph 100 includes a fused silica (FS) prism 140. The resulting range of wavelengths delivered to the plane 195 is from about 180 nm to above 1.1 microns. As used herein, "about" means plus or minus 10% difference in any measurements. If prism 140 is made of CaF2, one limit of the wavelength range at the plane 195 can be extended down to about 150 nm. Another embodiment can include a BK7 glass prism 140. BK7 has higher dispersion than that of FS or CaF2, but it does not transmit light below about 340 nm. The wavelength range of the echelle spectrograph 100 in this case would be from about 340 nm to about 1.1 microns; at the same time, the spectral order separation is larger when using BK7 prism. A taller entrance aperture 101 can then be used to increase the throughput of this embodiment of the instrument containing a BK7 glass prism 140.

Many optical materials including FS, CaF2 and glass have good transmission above 1.1 microns. However, silicon based sensors cannot detect wavelengths longer than 1.1 microns, so spectrographs are limited to a maximum wavelength of 1.1 microns when using silicon-based sensors. When using InGaAs or other infrared sensitive detectors, the TMA-based echelle spectrograph can have good sensitivity beyond 1.1 µm. The long-wavelength limit is determined by the detector sensitivity, and the transmission characteristics of the prism and the corrective field lens. The wavelength range of an echelle spectrograph is also dependent on the useable area of the image plane. The larger the image plane, the more spectral orders can be located on the sensor, resulting in larger wavelength coverage.

FIG. 1 shows light 240 exiting prism 140 and then directed onto the folding mirror 150. In certain embodiments, the folding mirror 150 is configured to rotate only about the first axis 152 by 42 degrees as shown in FIG. 1. In other embodiments, folding mirror 150 is first configured to rotate about the first axis 152 and then is configured to rotate about the second axis 154 in the plane of the mirror. FIG. 2 shows an embodiment where the fold mirror has been rotated about both the first axis 152 and the second axis 154. It has been rotated −5 degrees about axis 152 and then rotated by +45 degrees about the second axis 154.

Referring again to FIG. 1, the folding mirror 150 is tilted in such a way as to prevent obstructions to light beams 250, 260, 270, and 280 that propagate towards and between the mirrors of the TMA. Further, the folding mirror 150 is disposed at such an angle as to present no optical obstruction to other spectrograph components. As illustrated in FIG. 2, by rotating the folding mirror 150 about both axes 152, 154 in the plane of the mirror, the volume of the echelle spectrograph 100 can be decreased to create a more compact design. FIG. 3 shows the location of a parent vertex axis 322, which is defined as the vertex axis of the full-sized parent mirrors (only portions of the full-sized parent mirrors are shown in the figures) of each of the three mirrors within the TMA. The off-axis primary mirror 160, the off-axis secondary mirror 170, and the off-axis tertiary 180, which are respectively subsections of each one's parent mirror, substantially share the TMA parent vertex axis 322. "Substantially share" is defined as following: in some embodiments, the primary mirror 160, the secondary mirror 170, and the tertiary mirror 180 shares the parent vertex 322; and in other embodiments, the secondary parent vertex axis can be tilted +1.0 degree to about −1.0 degree relative to the parent vertex axis 322. Alternatively or in addition, the parent vertex axis 322 and the secondary parent vertex axis can be separated (translated) with respect to one another by as much a +2.0 mm to −2.0 mm in X or Y directions and still be considered to be "substantially shared." Such tilt can help cancel residual astigmatism in the TMA for a sharper focus at image plane 195. The compact design in FIG. 2 allows the camera focusing optics 320 to be located closer to the parent vertex axis 322 which minimizes spectrograph aberrations, as one skilled in optical design appreciates. In certain embodiments, the primary mirror 160 can be located closer to the tertiary mirror 180, without causing obstructions to rays 260 passing between the primary mirror 160 and secondary mirror 170 by the fold mirror 150. The rays 260 approaching the secondary mirror 170 have a shallow angle relative to the parent vertex axis 322 and rays 280 departing the secondary mirror 170, also have a small angle relative to the parent vertex axis 322 as rays 280 approach the tertiary mirror 180. The shallower the angle of rays relative to the TMA vertex axis, the better and sharper the image quality at the image plane 195, as those skilled in the art will appreciate.

Figure 5A:
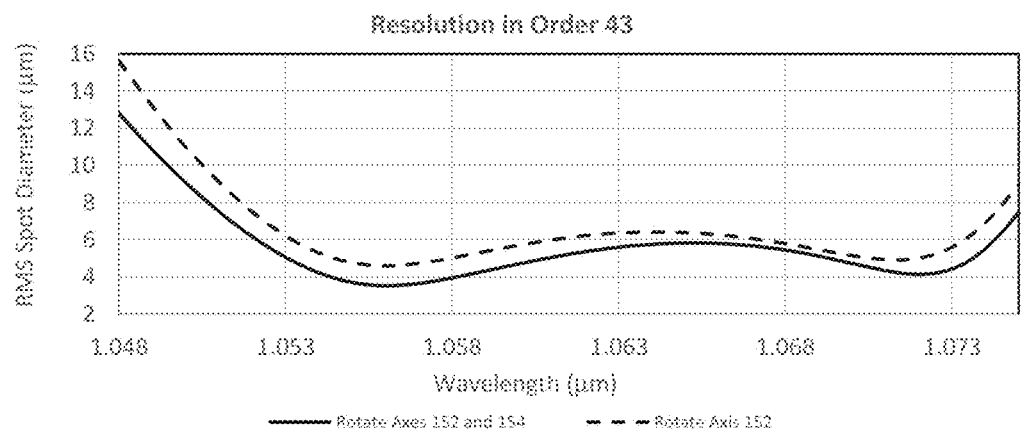
FIGS. 5A, 5B and 5C illustrate the effect of the fold mirror rotation on resolution for the echelle spectrograph.
Figure 5B:
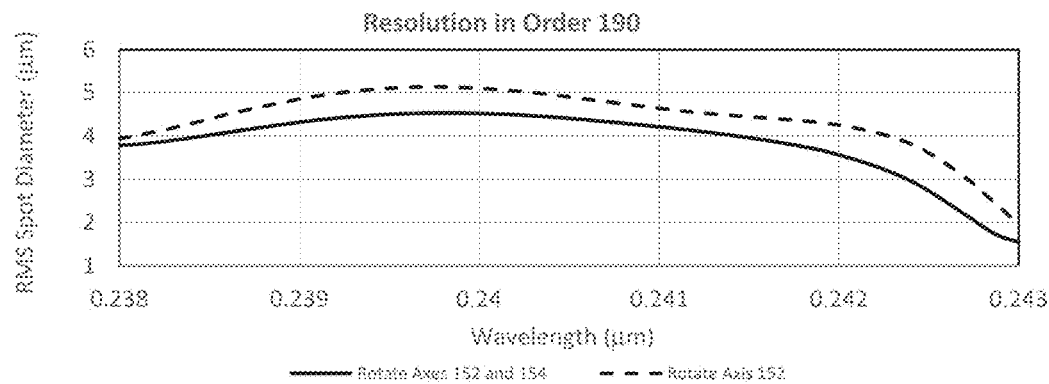
Figure 5C:
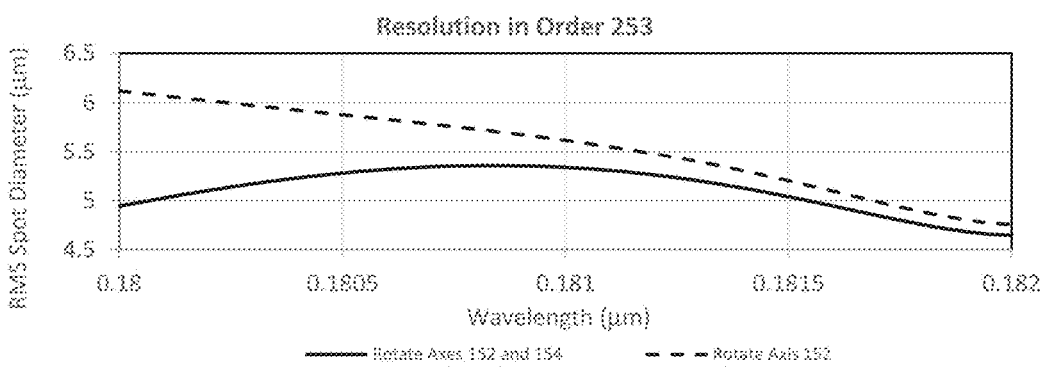

As an example of the image resolution improvement, FIGS. 1 and 2 show similar optical designs with fold mirror 150 rotated about axis 152 in FIG. 1 and with the fold mirror axis 150 rotated about both 152 and 154 axes in FIG. 2. The resulting image quality for the two embodiments are shown in FIGS. 5A-5C, which show the RMS spot diameter across 3 different orders on the image plane. The RMS spot diameter is a measure of the smallest focal spot diameter that can be measured on the image plane (excluding diffraction effects) and it is a measurement of the optical aberrations in the system. The smaller the RMS spot diameter, the better the spectral resolution. Referring to FIGS. 5A-5C, the dashed lines represent the RMS spot diameter obtained with the embodiment of the spectrograph wherein the fold mirror 150 was rotated about axis 152 and the solid lines represent the RMS spot diameter obtained with the embodiment of the spectrograph wherein the fold mirror 150 was rotated about both axes 152 and 154. The solid lines show decreased RMS spot diameter under different diffraction orders compared to the dashed lines, thus, the embodiment of the spectrograph illustrated in FIG. 2 has better spectral resolution than the embodiment of the spectrograph illustrated in FIG. 1. The improved resolution is achieved because there is less interference among mirrors 150, 160, 170, and 180 and their associated rays 250, 260, 270 and 280 so mirrors 150, 160, 170, and 180 can be disposed closer together. Since the mirrors 150, 160, 170, and 180 are closer together, the mirrors are closer to on-axis relative to their substantially shared TMA parent vertex axis 322, shown in FIG. 3.

Further, as shown in FIG. 1, light 240 is reflected by the folding mirror 150 to form a beam of light 250. For any given wavelength, this beam remains collimated. However, light at different wavelengths reflects off of the folding mirror 150 at slightly different angles because of the dispersion by grating 130 and prism 140.

Light 250, as shown in FIG. 3, is incident on the camera focusing optics. The first mirror of the TMA portion of the camera focusing optics is the primary mirror 160. In the embodiment displayed in FIG. 2, the primary mirror 160 has a radius of curvature of about 604.372 mm (concave) and a conic constant of −0.63642 (rendering this mirror to be ellipsoidal in shape).

Reflected light 260 in FIG. 1 converges upon propagation from the primary mirror 160 to an intermediate focus 165 and then diverges upon further propagation from the intermediate focus 165 towards the TMA's secondary mirror 170. In certain embodiments, an opaque baffle containing an aperture can be disposed at the intermediate focus 165 such that light 260 passes through this aperture in the baffle, and strikes the secondary mirror 170 afterwards. Such aperture serves to block most of stray light from reaching the image plane 195.

In the embodiment shown in FIG. 2, the secondary mirror 170 has a radius of curvature of 312.0 mm (convex) and a conic constant of 0. In such embodiment, therefore, the secondary mirror 170 is shaped as a spheroidal convex mirror. In other embodiments, the secondary mirror 170 comprises an ellipsoidal (0.0>conic constant >−1.0), parabolic (conic constant=−1.0) or hyperbolic (conic constant <−1.0) convex mirror.

Light 260 is reflected by the secondary mirror 170 and forms a diverging beam of light 270, which passes onto the TMA's tertiary mirror 180. In certain embodiments, the tertiary mirror comprises an ellipsoidal (0.0>conic constant >−1.0), spheroidal (conic constant=0), or oblate spheroidal (conic constant >0) concave mirror. In general, it is preferred to have the smaller value of the conic constant, because the smaller the conic constant (that is, the more of a negative value), the better the correction at the image plane (but the larger the mirror and spectrograph become).

In certain embodiments, the echelle spectrograph utilizes a spherical (spheroidal) mirror for the tertiary mirror 180. For example, in the embodiment in FIG. 2, the tertiary mirror 180 may have a radius of curvature of about 379.681 mm (concave) and a conic constant of 0. The spheroidal mirror is much easier to make than aspherical mirrors, resulting in lower fabrication costs.

Diverging reflected light 270 from the secondary mirror 170, as shown in FIG. 1, approaches the tertiary mirror 180. Light reflected from the tertiary mirror 180 converges as a light beam 280. The beam 280 is directed onto a field correcting lens 190 through a second stray light aperture 112. Light 280 passes through the first convex surface 192 of the field correcting lens 190. The light then exits the field correcting lens 190 through its second surface 194, which is concave, to focus onto the image plane 195. In other embodiments, the first surface 192 is spherical and concave and the second surface 194 is spherical and convex. In yet other embodiments, the first surface 192 is convex and the second surface 194 is flat. In certain embodiments such as FIG. 2, the first surface 192 is spherical and convex with a 149.396 mm radius of curvature. The second surface 194 (of the field correcting lens 190) is spherical and concave with a 405.573 mm radius of curvature (positive meniscus lens). Further, in certain embodiments, the field correcting lens 190 parent vertex axis is located on the parent axis shared by the TMA primary 160, secondary 170, and tertiary 180 mirrors.

The embodiment may be further complemented with a camera sensor located at the image plane 195. In certain embodiments, a sensor is a scientific, digital CCD, ICCD, CID, CMOS, InGaAs, HgCdTe or other optical detector used to collect image data of the light from an emitting source.

One way to change the f/number of the input optics of the echelle spectrograph 100 is to change the focal length of the collimator mirror 105. For purposes of this discussion, the f/number=1/(2×(sin θ)), where θ is a half angle of a cone of light passing through the entrance aperture 101. The numerical aperture (NA) for the entrance aperture 101 is defined as $NA_c = \sin(\theta)$, or equivalently, $$NA_c = \sin[\arctan\{D/(2 \times F_c)\}] \sim D/(2 \times F_c) \text{ when } F_c \gg D. \quad (2)$$

and, $$f_c/\text{number} = 1/(2 \times NA) \sim F_c/D \text{ when } F_c \gg D. \quad (3)$$

where D is the diameter (if circular) of aperture stop 110 and $F_c$ is the effective off-axis focal length of the collimator mirror 105. In the situation when the aperture stop 110 is non-circular, the NA and $f_c$/number can be generalized by an "averaged NA" or averaged $f_c$/number.

The $f_i$/number of the camera focusing optics is independent of the $f_c$/number of the collimator mirror. Equations 2 and 3 are modified to become, $$NA_i = \sin[\arctan\{D/(2 \times F_i)\}] \sim D/(2 \times F_i) \text{ when } F_i \gg D. \quad (4)$$

and, $$f_i/\text{number} = 1/(2 \times NA_i) \sim F_i/D \text{ when } F_i \gg D. \quad (5)$$

where $F_i$ is the effective focal length of the camera focusing optics and D is once again the diameter of the aperture stop. For clarity, the effects of anomorphic magnification introduced by the grating and prism have been ignored in these equations. In some embodiments when large blaze gratings are implemented, the anomorphic $f_i$/number, $NA_i$, and $F_i$ are location dependent on the image plane.

Broadband (<200-1100 nm wavelength coverage) echelle spectrographs discussed in related art typically contain $f_i/7$ ($NA_i = 0.07$) or larger $f_i$/number camera focusing optics. In contradistinction, the camera focusing optics of the echelle spectrograph 100 utilizes an $f_i/2$ optical system ($NA_i = 0.25$), in some embodiments. The high $NA_i$ value is approximately an order of magnitude improvement in light throughput compared to devices of related art (assuming similar resolution, wavelength coverage, and equivalent focal length of the camera focusing optics).

The total amount of light passing through the entrance aperture 101 is defined by the étendue (E) of the system at the aperture stop 110. At the aperture stop 110, E is proportional to the product of the area of the entrance aperture 101 and the square of the numerical aperture. Therefore, increasing either the numerical aperture of light passing through entrance aperture 101 or increasing the area of entrance aperture 101 increases total throughput (E) of the instrument. However, as those skilled in the art will appreciate, in general, the spectral resolution (defined by the full width at half maximum of a spectral emission line, FWHM) of an instrument is approximately proportional to the width of the entrance aperture 101 (when aberrations and diffraction effects are excluded).

As those skilled in the art will further appreciate, the light passing through the echelle spectrograph 100 contains multiple spectral orders that are spatially separated, or dispersed, as light passes through prism 140. Furthermore, the height of entrance aperture 101 on the image plane is preferably smaller than the distance between the neighboring spectral orders at image plane 195 to reduce or even eliminate cross-talk between the spectral orders. Therefore, the size of the entrance aperture 101 is limited in both height and width to provide for good spectral order separation and high spectral resolving power (wavelength/FWHM) at the image plane 195. The preferred way to increase throughput is to increase the numerical aperture (or, decrease the f/number).

It is important to note that the light source is disposed in optical (radiative) communication with (that is, optically coupled to) the entrance aperture 101. Furthermore, to maximize throughput of light, the f/number of the optics associated with the light source that is externally coupled to entrance aperture 101 shown in FIG. 1 is preferably matching the $f_c$/number of the collimator mirror defined by $F_c$ and D (see equations 2 and 3). Each embodiment of the external optical coupling to the entrance slit can have a very different f/number. For example, a typical effective f/number of an optical fiber is f/2.3 (NA=0.22) and the f/number of a telescope can be f/16 or higher.

In certain embodiments, echelle spectrograph 100 can have collimator mirror 105 of a different focal length while maintaining the same mirror diameter and aperture stop D. For example, if the focal length of collimator mirror 105 is doubled, then the $f_c$/number of the collimator as defined by Equation 3 is increased by a factor of about two ($NA_c$ is reduced in half) if D remains unchanged. The magnification provided by the echelle spectrograph 100 is defined as a ratio of the effective focal length of the camera focusing optics (Fi) to the off-axis effective focal length of the collimator mirror (Fc):

$$M=Fi/Fc \quad (6)$$

When the value of $F_c$ is doubled, the value of M is halved. The image of entrance aperture 101 projected onto image plane 195 at a given wavelength (or equivalently, the FWHM of a spectral emission line) is then approximately half the size as with the original embodiment. It is therefore possible to double the dimensions of the entrance aperture 101 (in both height and width) to preserve the total throughput (or étendue E) of the echelle spectrograph 100 without degrading spectral resolution or changing any of the optics besides the collimator mirror.

The echelle spectrograph 100 can be configured to match any light source from approximately f/2 to >f/16 while maximizing étendue by simply changing Fc of the collimator mirror and the size of the entrance aperture 101. At the same time, the spectral resolving power (wavelength/FWHM) and diffraction order overlap remains unchanged. The image quality and order location at image plane 195 also remains unchanged as long as entrance aperture 101 is at the correct location (with the appropriate size) and D remains unaltered.

The field correcting lens 190 adds two more corrective optical surfaces when optimized with the other three TMA mirror surfaces for a total of 5 corrective surfaces. After optimization, the effective focal length ($F_i$) of the camera focusing optics can be increased as compared to that of a design without the field correcting lens. This longer $F_i$ results in higher spectral resolution for a fixed size of the spectrograph. A field correcting lens typically improves field curvature at the image plane when it is added to an existing optical design. The TMA by design may not have field curvature. When simultaneously optimizing the first surface 192 and the second surface 194 of the field correcting lens 190, and the TMA mirrors (160, 170, 180), most camera focusing optics aberrations (spherical, astigmatism, coma, field curvature, etc.) are significantly reduced. For example, using a design without the field correcting lens 190 and a narrow entrance aperture 101, the average minimum RMS slit image diameter that can be focused on the image plane 195 is 5.4 microns using a 35 mm diameter aperture stop ($f_i$/5.4 camera focusing optics). Including the field correcting lens 190 in a spectrograph with similar $F_i$ and aperture stop, the average RMS spot diameter becomes 3.6 microns. On average, the aberrations have been reduced 33% by including the field correcting lens. Using a 50 mm ($f_i$/3.8) aperture stop 110, the average minimum RMS slit image diameter becomes 16.6 microns for the spectrograph without the field correcting lens 190, making it unusable for many applications. The spectrograph with the field correcting lens 190 has a very good 6.4 micron average minimum RMS spot diameter across the image plane 195, in all orders. In this example, including the field correcting lens 190 in the spectrograph decreased aberrations on average by 61.5%. Moreover, the useable size of a sensor is increased, i.e., a much larger corrected area at the image plane 195 is achieved. This results in higher throughput and resolving power since higher prism and grating dispersion can be utilized. A further advantage of using the field correcting lens 190 is that the distance between the fold mirror 150 and the secondary mirror 170, and the distance between the secondary mirror 170 and the image plane 195 are increased compared to a spectrograph without the field correcting lens 190. Thus obstructions of rays 260 by the flat mirror 150 and obstructions of beam 280 by the secondary mirror 170 are minimized. For example, a 50 mm aperture stop 110 would require the fold mirror 150 and secondary mirror 170 to be so large that they would obstruct each other, making a design with a 50 mm aperture stop 110 impractical.

Figure 6:
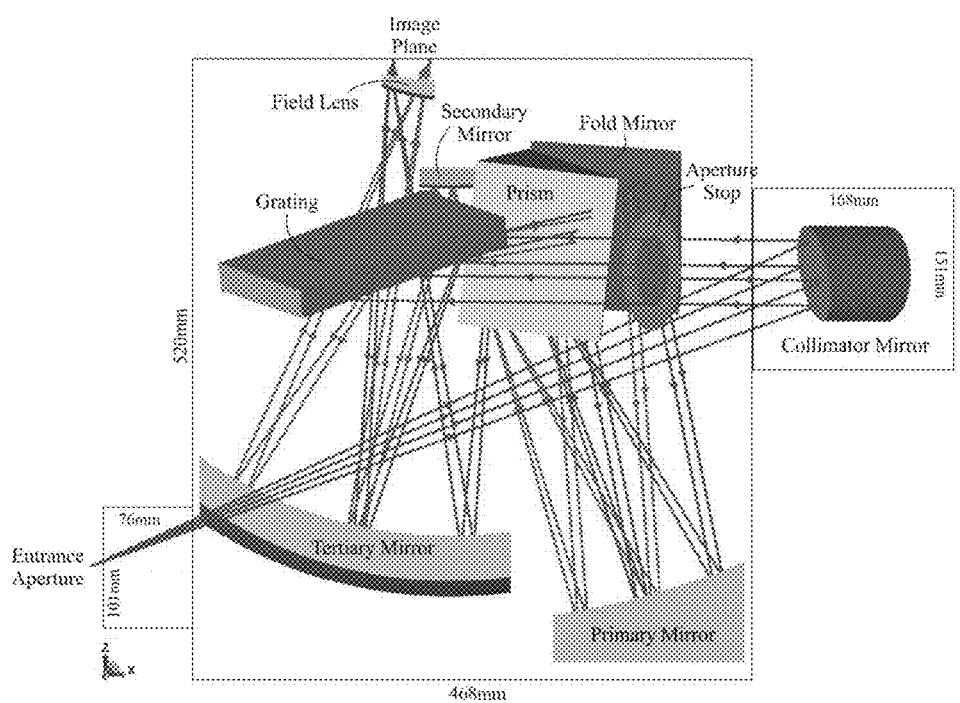
FIG. 6 illustrates the embodiment of the echelle spectrograph in FIG. 2 with dimensions.
Figure 7:
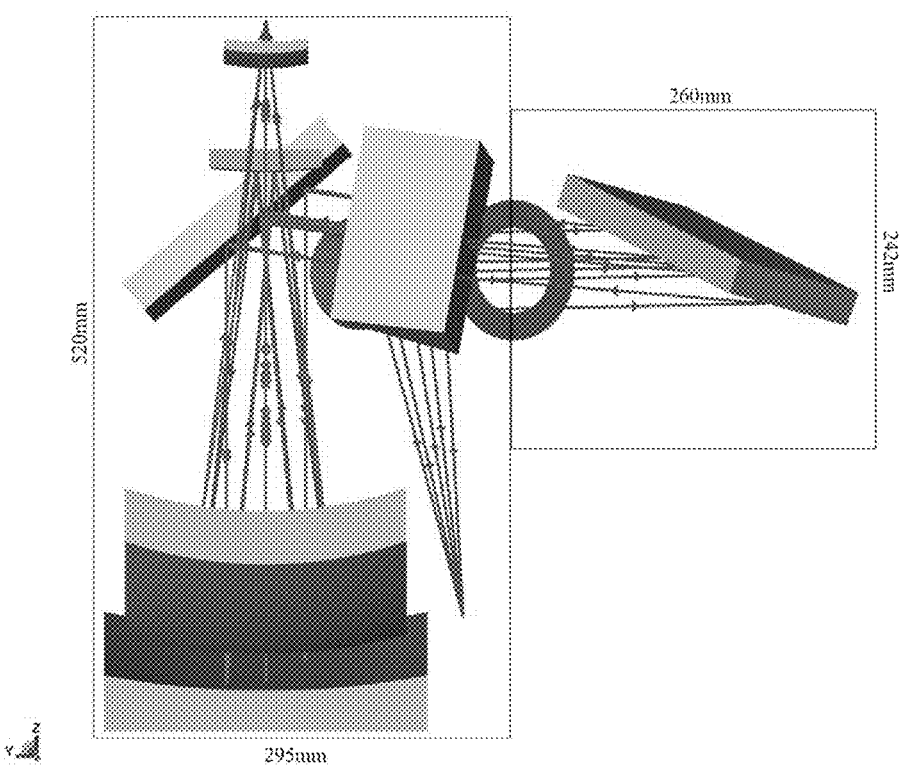
FIG. 7 shows a different perspective of the embodiment of the echelle spectrograph in FIG. 2 with dimensions.

A longer $F_i$ of the echelle spectrograph 100 results in higher spectral resolving power (wavelength/FWHM). In certain embodiments, the spectral resolving power of the echelle spectrograph 100 exceeds 200,000 for a field portable instrument. The typical value of the resolving power for a field portable conventionally-configured echelle spectrograph is on the order of a few thousand. FIG. 6 (a perspective view as seen along y-axis) and FIG. 7 (a perspective view as seen along x-axis) show the dimensions of the instrument with $f_i$/3.8 camera focusing optics and resolving power of 200,000.

Moreover, because the spectral orders are located spatially further apart from one another, due to the larger useable size of the sensor, a larger entrance aperture 101 can be used without causing interference between the adjacent diffraction orders. For example, in one embodiment that does not contain (is devoid of) the field correcting lens 190, the maximum size of the entrance aperture 101 is about 25 microns without adjacent spectral order cross-talk. When a field correcting lens 190 is employed, however, the maximum size of the entrance aperture 101 can be about 56 microns without causing significant order cross-talk. Employing the field correcting lens 190, therefore, allows a combination of better spectrograph throughput (taller slit) and better resolving power (higher dispersion characteristics).

Figure 8:
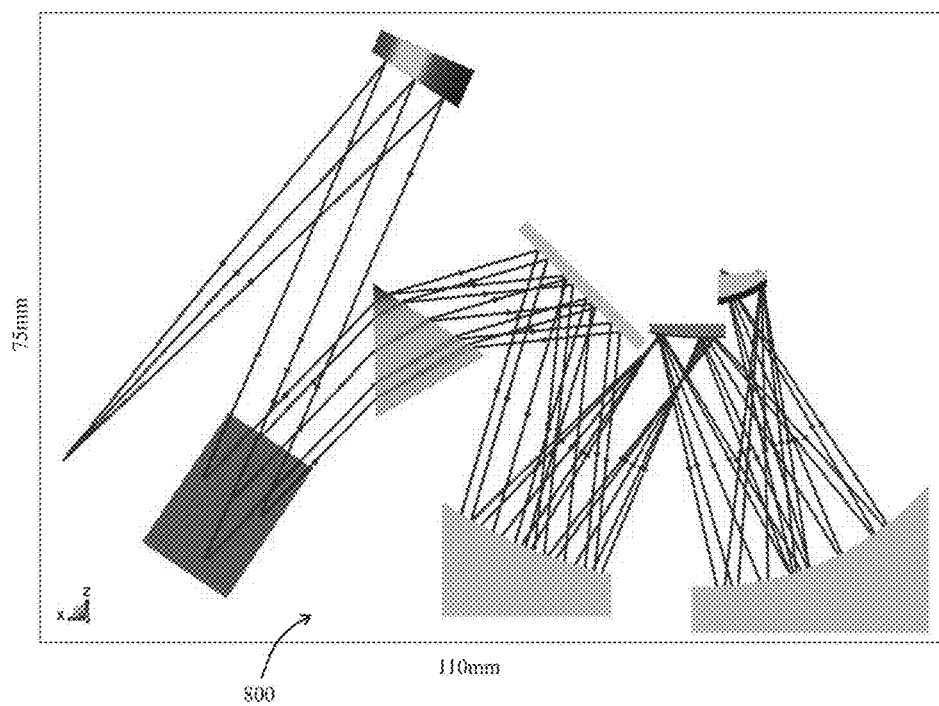
FIG. 8 illustrates another embodiment of the echelle spectrograph with different dimensions.
Figure 9:
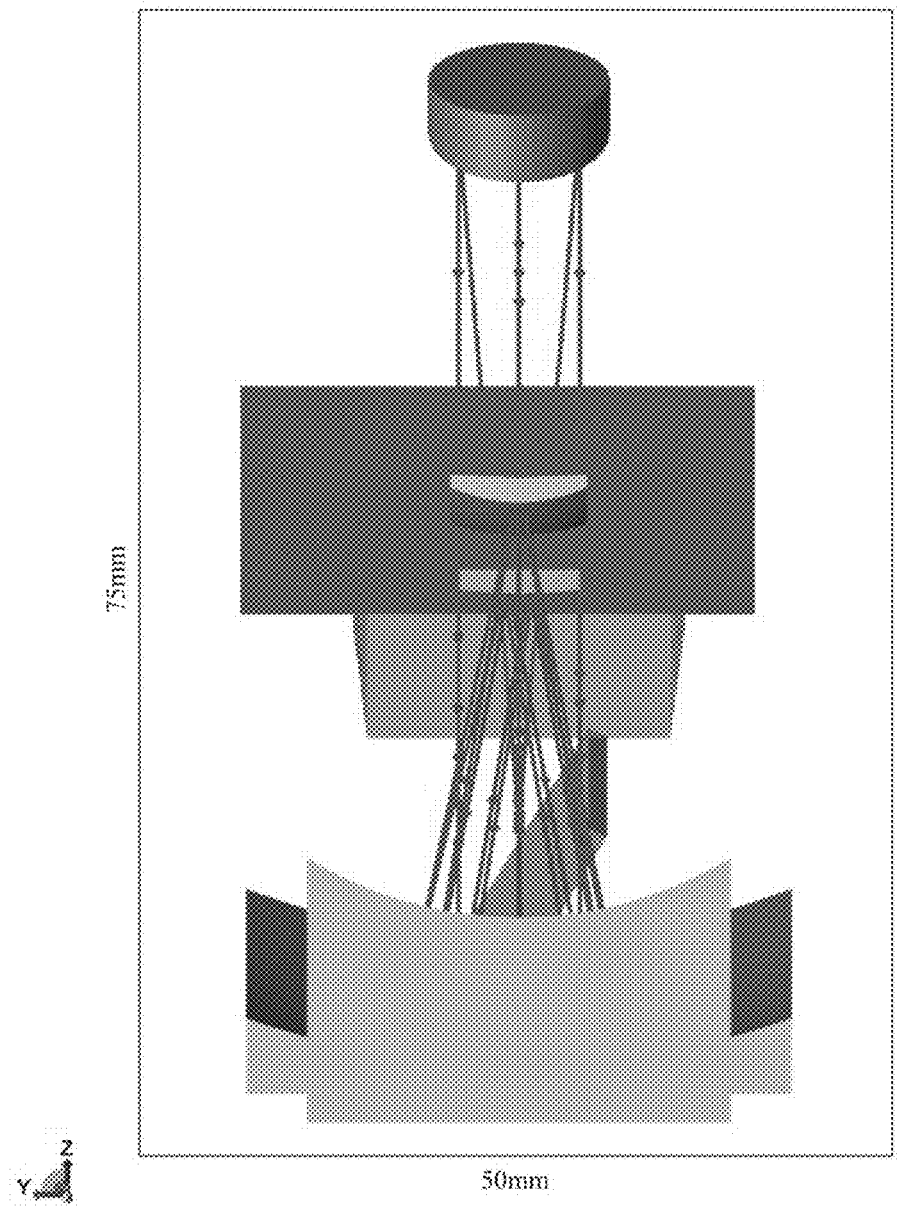
FIG. 9 shows a different perspective of the embodiment of the echelle spectrograph in FIG. 8.
Figure 10:
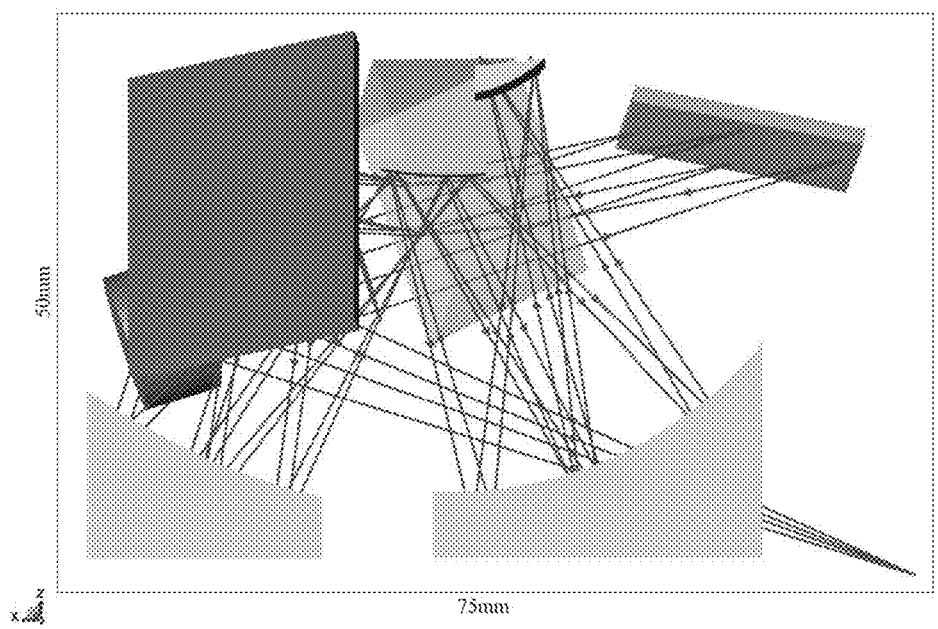
FIG. 10 illustrates yet another embodiment of the echelle spectrograph with different dimensions.
Figure 11:
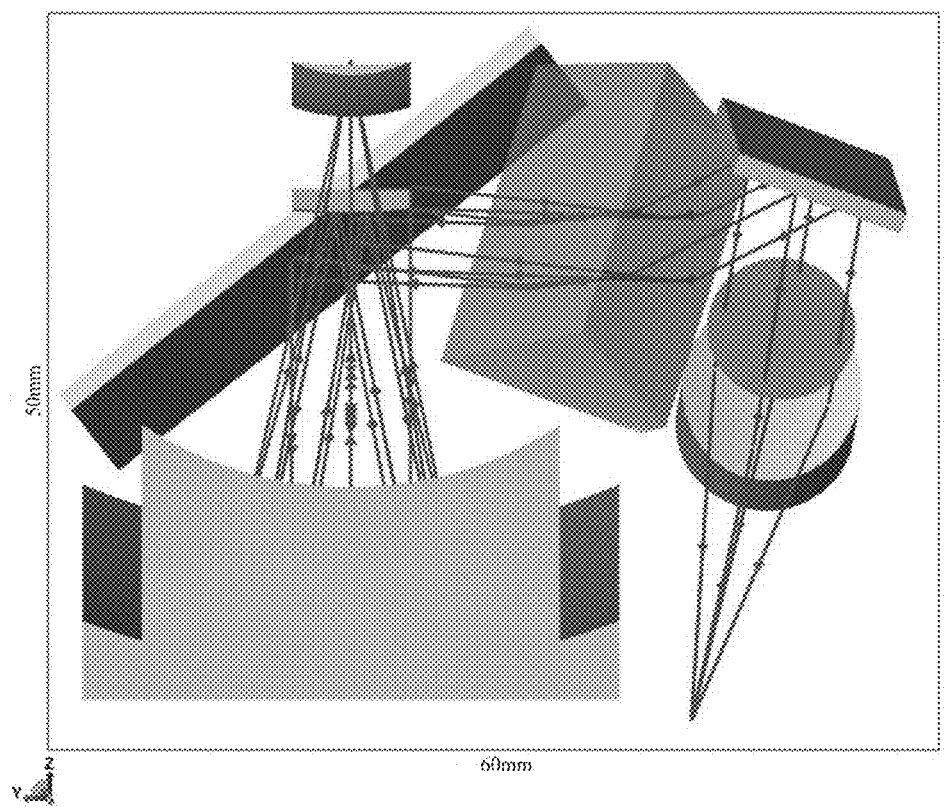
FIG. 11 shows a different perspective of the embodiment of the echelle spectrograph in FIG. 10.

In certain embodiments, FIG. 8 (a view in the XZ plane) and FIG. 9 (a view in the YZ plane) show the design and dimensions of a handheld field lens-corrected TMA echelle spectrograph with all of the optics aligned in a single plane with the fold mirror rotated about the axis perpendicular to the plane of the page on FIG. 8. The dimensions of the instrument 800 are 110 (l)×50 (w)×75 (h) mm. This handheld design can achieve a spectral resolving power of higher than 10,000 with complete wavelength coverage in the spectral range from 180 to 1100 nm, when the appropriate camera is used. FIG. 10 (a view in the XZ plane) and FIG. 11 (a view in the YZ plane) show a similar handheld echelle spectrograph with a 10,000+ resolving power and the 180-1100 nm range of the wavelength coverage, with the fold mirror axis tilted around both axis, which facilitates the reduction of the volume of the device. The dimensions of this instrument 800 could be 75 (l)×60 (w)×50 (h) mm. The folded echelle spectrograph 800 also has better aberration correction than the embodiment with the fold mirror tilted around just the axis perpendicular to the plane of the page. Either design has an order of magnitude better resolving power than existing handheld spectrographs and in many cases, better throughput.

Figure 12:
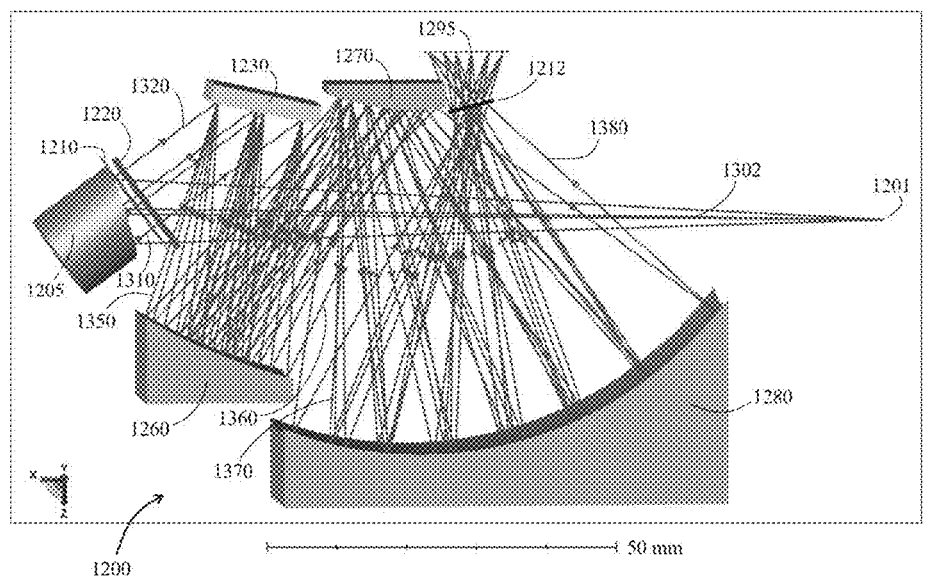
FIG. 12 illustrates an embodiment of a linear array or a 2-D imaging sensor with the use of the three mirror anastigmat (TMA), without a corrective field lens in the camera focusing optics component.
Figure 13:
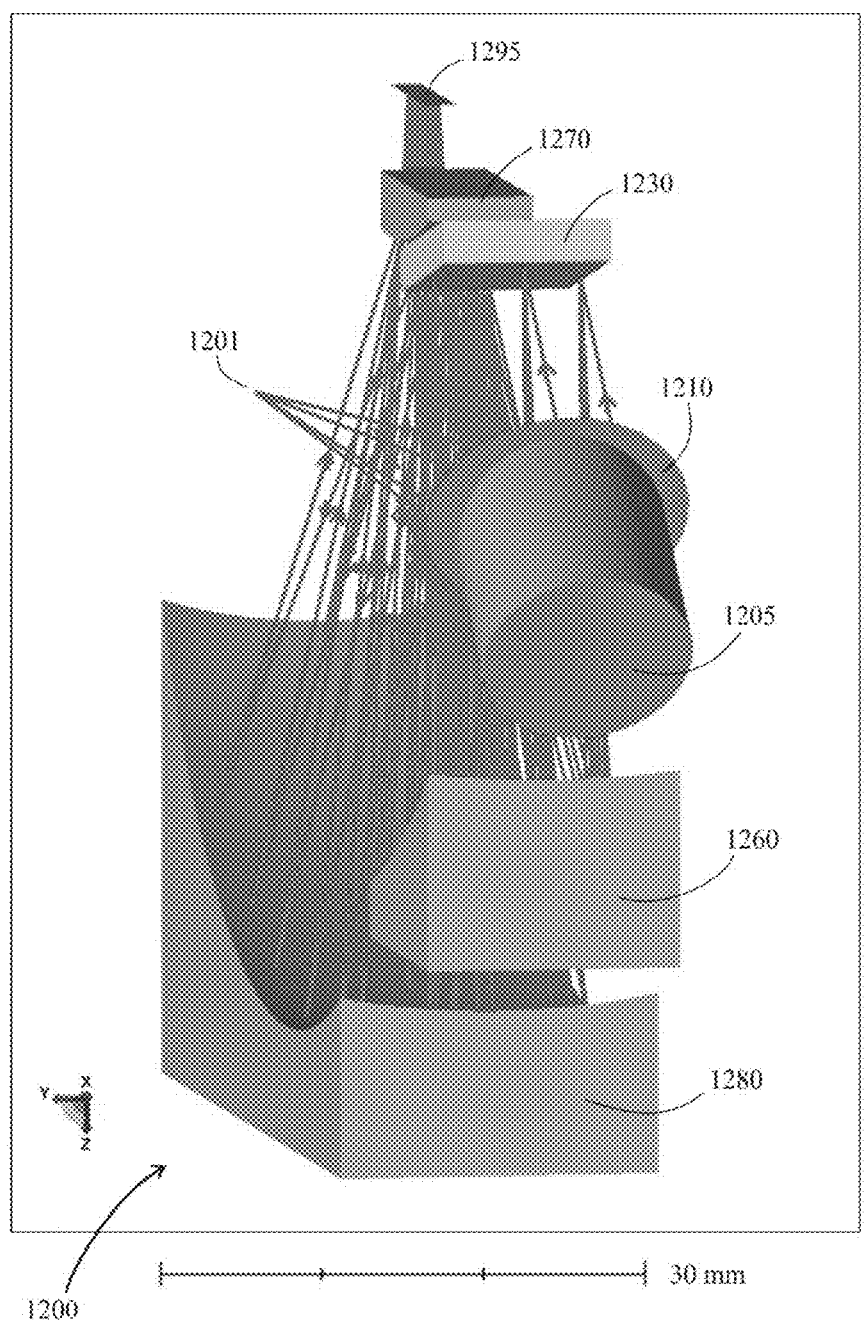
FIG. 13 shows a different perspective of the embodiment of the imaging or linear array spectrograph in FIG. 12.

FIG. 12 displays an embodiment of a spectrograph 1200 in the XZ plane. The spectrograph 1200 can be an imaging spectrograph or a linear array spectrograph. In certain embodiments, the spectrograph 1200 is a compact and handheld instrument. FIG. 13 displays the YZ plane of the spectrograph 1200 from FIG. 12. This embodiment is simpler than an echelle spectrograph and may be appropriate for use with Raman spectroscopy or other applications requiring a limited wavelength coverage with high resolution. This embodiment of the imaging spectrograph is similar to that of the echelle spectrograph illustrated in FIG. 1, however, the imaging spectrograph illustrated in FIG. 12 does not include a prism, a fold mirror, or a field correcting lens. It uses a standard $1^{st}$ order grating 1230 and not an echelle grating. A wavelength sorting filter 1220 is commonly inserted into the beam near an aperture stop 1210 although it can be located anywhere in the light path of the spectrograph. The order sorting filter blocks all wavelengths except the wavelengths associated with a single diffraction order to prevent order confusion on an image plane 1295. The wavelength coverage for this embodiment is 1.03 to 1.562 microns using a 12.8 mm long sensor and is designed for use with an InGaAs linear array sensor with 25×500 micron pixels.

The embodiment for the imaging spectrograph in FIG. 12 has light entering the spectrograph 1200 at entrance aperture 1201. Rays 1302 forming a cone of light from entrance aperture 1201 reflect from collimator mirror in a collimated beam 1310 toward aperture stop 1210. Rays 1320 travel through aperture stop 1210 and reflect and diffract from grating 1230. Grating 1230 can be a standard ruled grating used in $1^{st}$ order or other lower orders. It can also be a holographic, lithographic or other type of grating used in one of the lower grating orders, normally Order 1. The grating can either be a reflection or transmission grating. Rays 1350 travel from the grating to the TMA camera focusing optics. Rays 1350 reflect from the concave ellipsoidal primary mirror 1260 in a converging beam 1360. Light next reflects off the spheroidal convex secondary mirror 1270, forming a diverging beam 1370 that reflects from concave spheroidal tertiary mirror 1280. Rays 1380 pass through a $2^{nd}$ aperture stop 1212. The aperture stop 1212 is surrounded by baffles to further block stray light from reaching image plane 1295. Light travels through aperture stop 1212 and converges on image plane 1295. The aperture stop 1212 prevents stray light from reaching image plane 1295. This embodiment can produce RMS spot diameters 3 to 10 times smaller than comparable size and f/number Czerny-Turner type spectrographs commonly used in handheld instruments. The f/number of the spectrograph in this embodiment is about f/4 and the dimensions are 100 (l)×20 (w)×65 (h) mm. The average RMS spot diameter for this embodiment is 18.6 microns which is smaller than a pixel width of 25 microns.

Figure 14A:
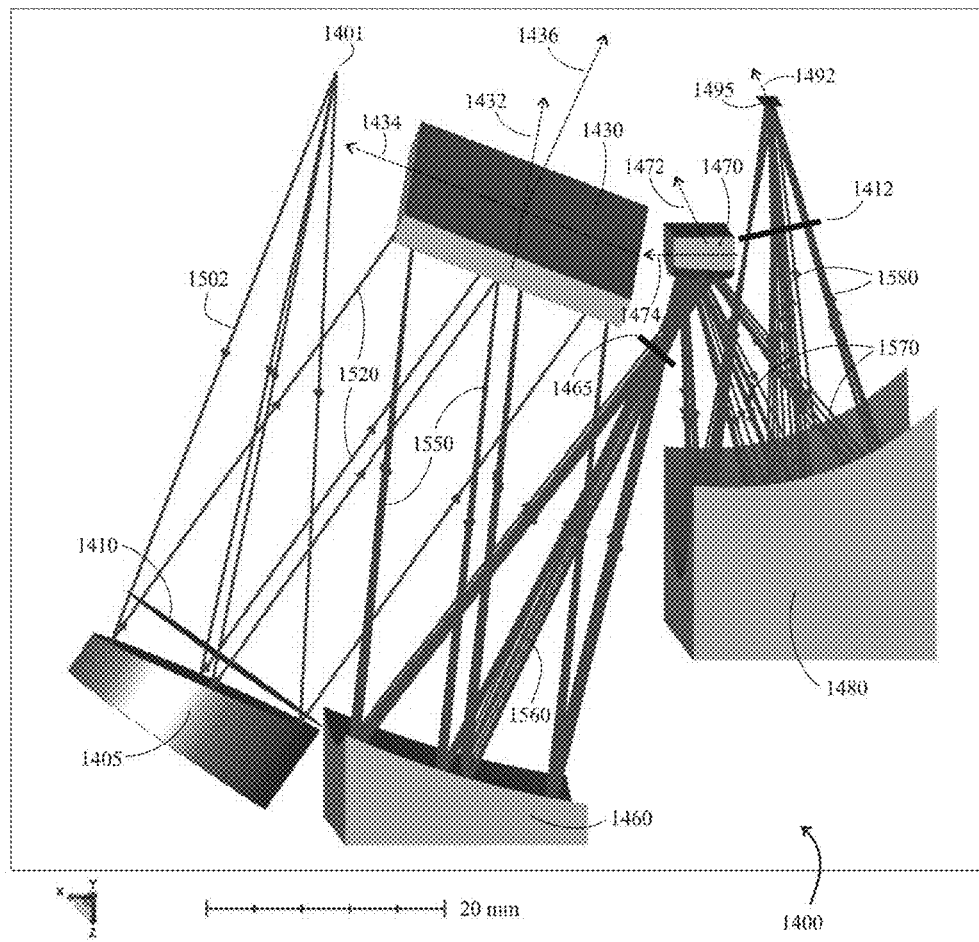
FIG. 14A is a different embodiment of a linear array or a 2-D imaging sensor whereas the grating has been rotated 90 degrees about an axis that is perpendicular to a plane of a grating, thereby resulting in a change of a general direction in which the diffracted light is spatially dispersed.
Figure 15:
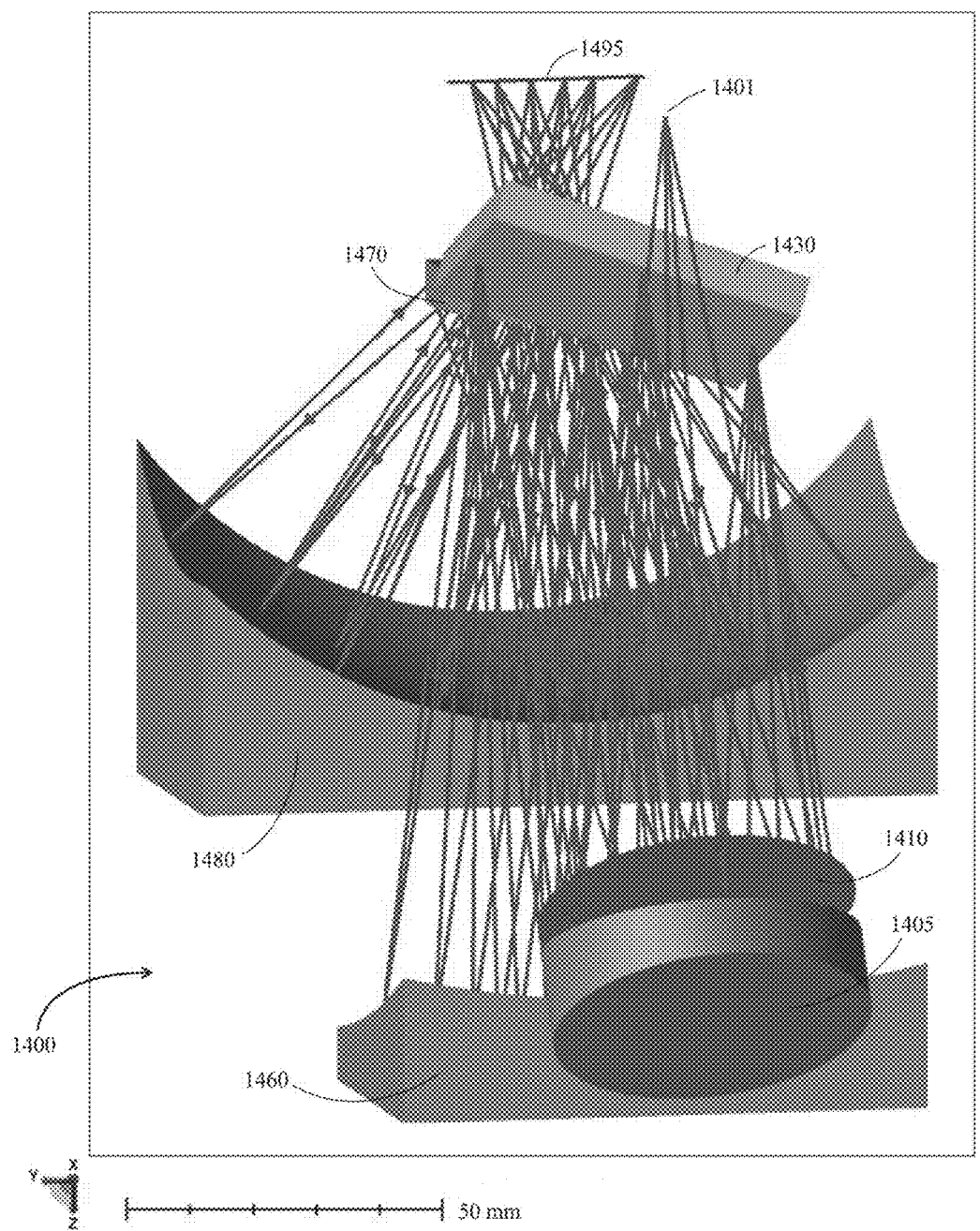
FIG. 15 shows a different perspective of the embodiment of the imaging or linear array spectrograph illustrated in FIG. 14A.

Referring to FIGS. 14A and 15, the grating 1430 is rotated 90 degrees about an axis 1436 perpendicular to the plane of the grating, hence the light dispersion occurs along the YZ plane instead of the XZ plane. Thus, spectrograph 1400 can be configured as an imaging spectrograph or as a linear array spectrograph. FIG. 15 shows the YZ plane of the spectrograph 1400. As shown in FIG. 15, the primary mirror 1460, secondary mirror 1470 and tertiary mirror 1480 are very wide in the YZ plane or along a direction of dispersion of light upon interaction with the grating (a dispersion direction), but narrower in the XZ plane shown in FIG. 14A. This change in width of the optical components results in reduction of spatial interference or obstruction among grating 1430, primary mirror 1460, secondary mirror 1470 and tertiary mirror 1480. Therefore, the mirrors can be much faster, with lower f/numbers. The throughput of spectrograph 1400 corresponds to, in one implementation, f/2.3 and the dimensions are 75 (l)×48 (w)×63 (h) mm. The average RMS spot diameter is 7.7 microns at f/4, and 15.7 microns at f/2.3. The spectrograph 1400 has nearly 4× higher throughput for the same average spot diameter on the image plane as compared to the spectrograph 1200. However, the spectrograph 1400 is wider in the YZ plane than the embodiment illustrated in FIGS. 12 and 13.

Figure 14B:
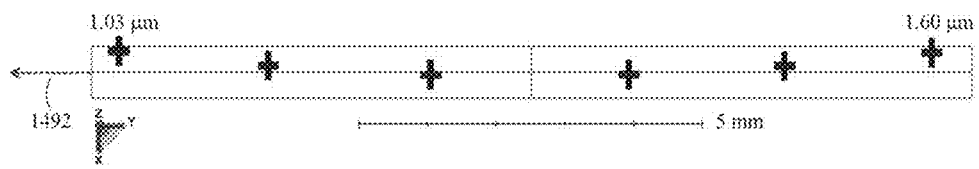
FIG. 14B shows the location of 6 wavelengths along a 500 µm×12.8 mm linear array sensor for the embodiment in FIG. 14A.
Figure 16A:
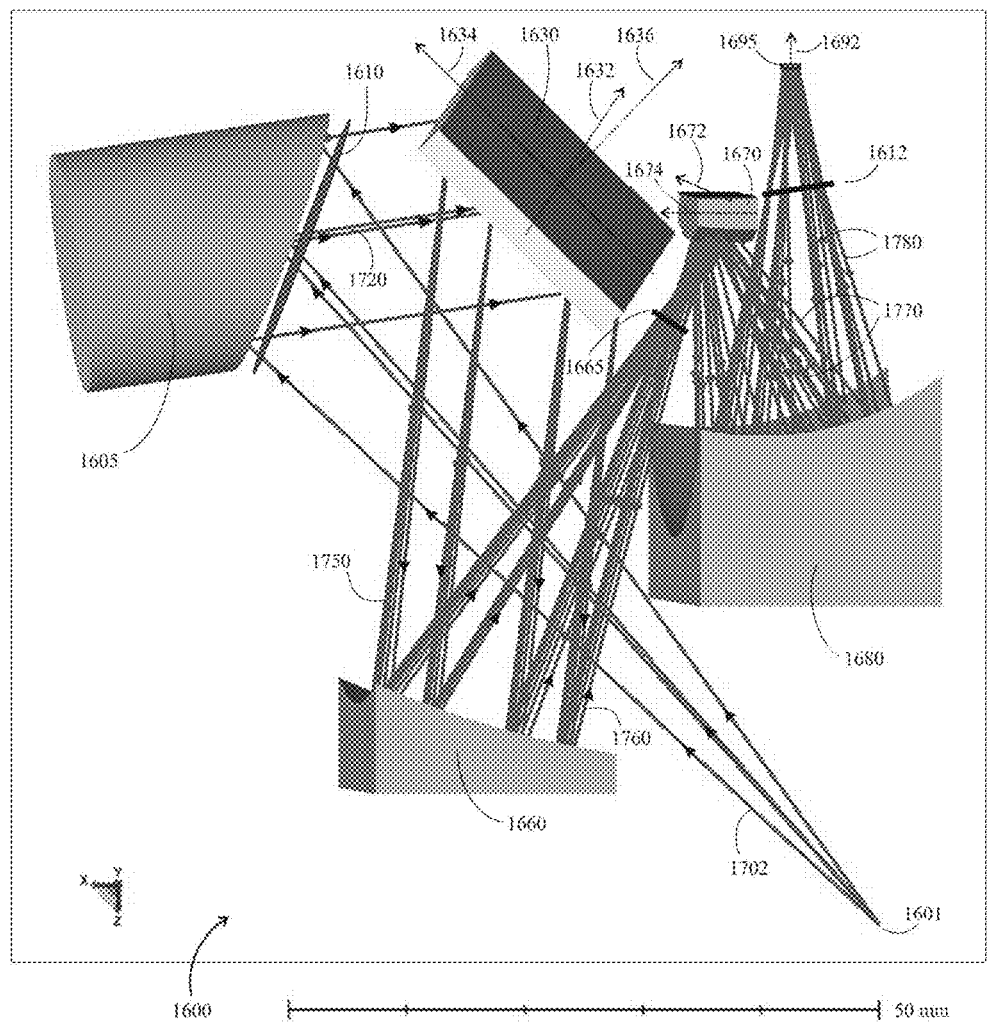
FIG. 16A and FIG. 16B illustrate an embodiment wherein the grating is rotated to cancel the geometric distortion on the image plane, as shown in FIG. 16B.
Figure 16B:
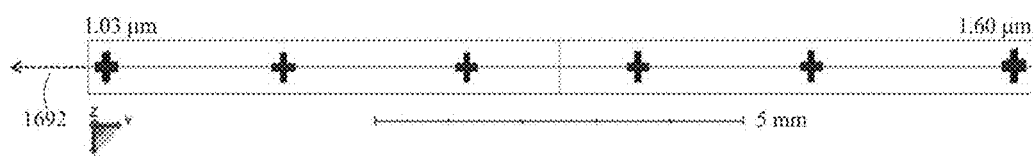

FIG. 16A, showing the embodiment of a spectrograph 1600, is a similar design to the spectrograph 1400 depicted in FIG. 14A. However, the locations of entrance aperture 1401 in FIG. 14A and 1601 in FIG. 16A are different to accommodate different tilts of the diffraction grating. In FIG. 14A, diffraction grating 1430 is rotated −14 degrees about the Y-axis 1432, and then −20 degrees about the X-axis 1434. In FIG. 16A, the diffraction grating 1630 is rotated −37 degrees about the Y-axis 1632, and then −24.5 degrees about the X-axis 1634. The rotations about the X-axes 1434 and 1634 corresponded approximately to the blaze angles of the diffraction gratings 1430 and 1630. "Approximately" is defined as that the rotations about the X-axes 1434 and 1634 are not necessarily exactly at the blaze angles of the gratings. The blaze angle is optimized to maximize efficiency for the wavelength of the used light and spectral resolving power. The rotation about the Y-axes allows flexibility in the location of the collimator mirrors 1405 and 1605. A feature of the rotation about the Y-axes is the amount of geometric distortion added to the image plane. FIG. 14B illustrates 6 different wavelengths ranging from 1.03 μm on the left end of the sensor up to about 1.6 μm on the right side of a linear array sensor that is 12.8 mm long by 500 μm wide. Note that the wavelengths do not track the centerline axis 1492 of the sensor, and the wavelengths fall upon a curved path. Wavelengths 1.03 μm and 1.60 μm barely strike the active portion of the linear array sensor. The curvature resulted from geometric distortion created by a combination of off-axis camera focusing optics and a grating rotated about the Y-axis. In FIG. 16B, all wavelengths are aligned along the centerline axis 1692. The geometric distortion introduced by the camera focusing optics was mostly canceled in spectrograph 1600 by the inverse distortion introduced by increased rotation of the grating Y-axis 1632. Adjusting the grating rotation is a very useful tool since it allows a linear array to be used at the image plane without light from the slit image missing the sensor. It is equally important to imaging and echelle spectrographs that make use of 2-D sensor arrays since it is much easier to track orders in software when those orders are linear across the sensor instead of parabolic or some other curvature.

In certain embodiments, as with the echelle design spectrographs, imaging and linear array spectrograph embodiments are improved by offsetting the entrance aperture 1401 in FIGS. 14A and 15 in X and Y with respect to the collimator parent vertex axis 312 up to approximately 3 millimeters, but typically less than 300 microns on short focal length collimators (<100 mm focal length). Image quality are improved by either offsetting secondary mirror 1470 axis up to a few hundred microns in X and Y, or by rotating the secondary about axis 1474 (X) and axis 1472 (Y) up to a few 10ths of a degree. As those skilled in the art of optical design will appreciate, tilting a spheroidal mirror has the same effect on aberrations as offsetting the mirror location.

Figure 17:
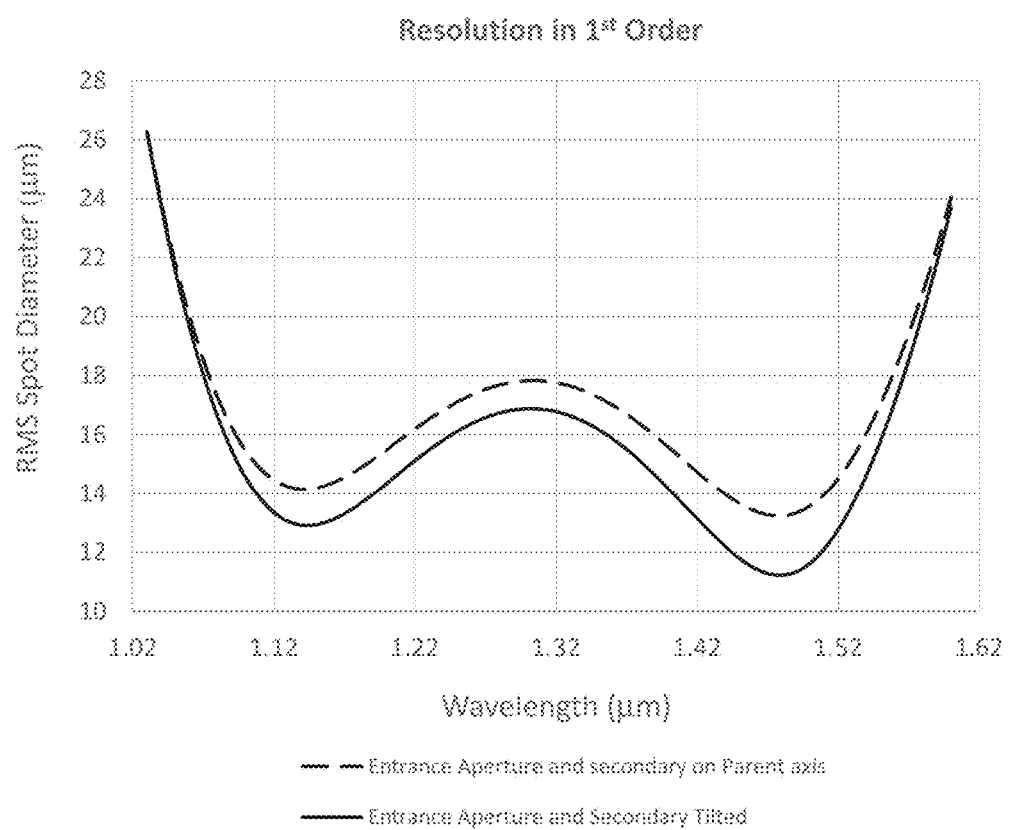
FIG. 17 illustrates the difference in root mean square (RMS) spot diameter when offsetting the entrance slit from the nominal parent vertex location and by tilting the secondary mirror.

Another improvement in the design of echelle, imaging and linear array spectrographs were achieved by offsetting the entrance aperture in X and Y dimensions while simultaneously tilting the secondary mirror of the TMA. In an exemplary embodiment, FIG. 17 compares the RMS spot diameters produced at the image plane 1495 in FIGS. 14A and 14B by allowing the entrance aperture 1401 to be offset in X and Y dimensions while simultaneously tilting the secondary mirror 1470 to optimize (minimize) aberrations. The offset of the entrance aperture was X=−179.6 μm, Y=215.3 μm relative to the parent collimator focus location. The secondary mirror tilt about the X-axis 1474 is 0.088 degrees and the tilt about the Y-axis 1472 is 0.234 degrees.

Figure 18:
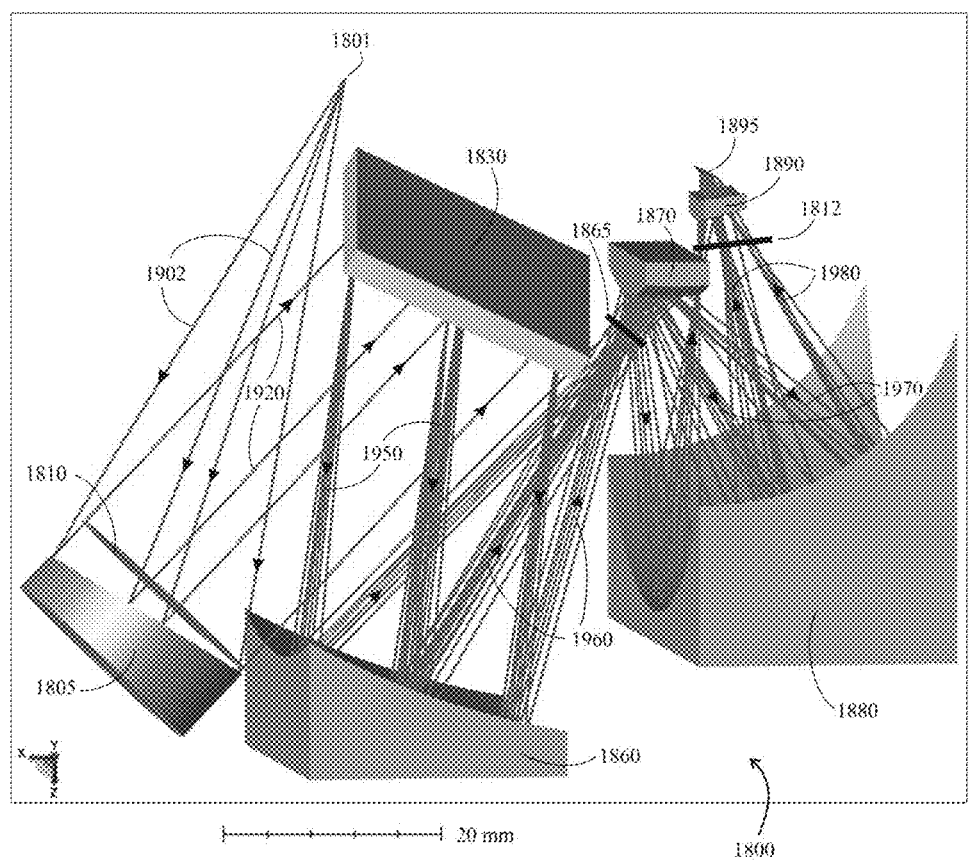
FIG. 18 illustrates yet another embodiment of a linear array or a 2-D imaging sensor including a field correcting lens.
Figure 19:
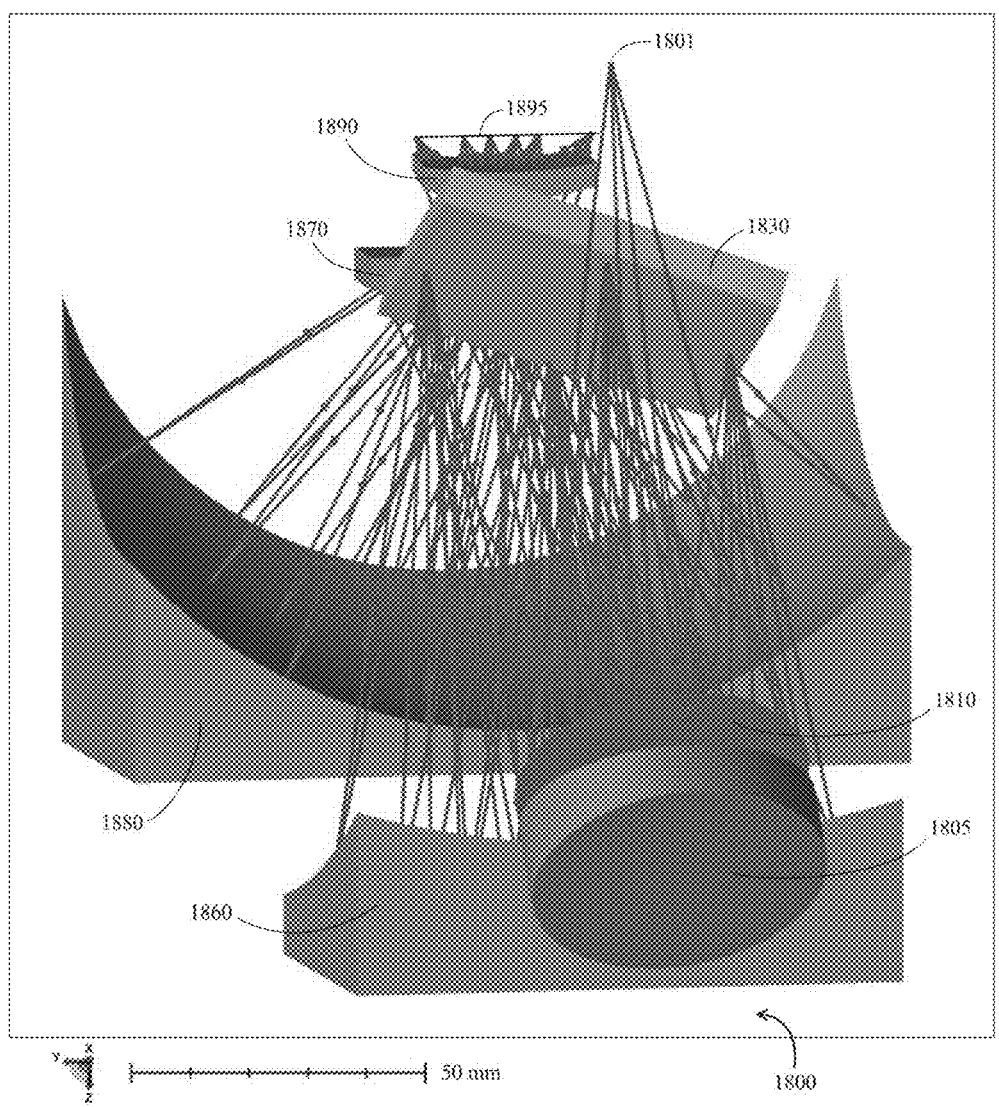
FIG. 19 shows a different perspective of the embodiment of the imaging or linear array spectrograph illustrated in FIG. 18.

FIGS. 18 and 19 illustrate another embodiment of a spectrograph 1800, with FIG. 19 showing the YZ plane. The spectrograph 1800 can be an imaging spectrograph or a linear array spectrograph, and it comprises a positive meniscus field correcting lens 1890. The dimensions of the spectrograph 1800 are 88 (l)×58 (w)×40 (h) mm. The field correcting lens 1890 improves the throughput to f/1.5 while the volume of the instrument is similar to embodiments without the field lens. The average RMS spot diameter is 18.0 microns at f/1.5, and 7.1 microns at f/2.3. The wavelength coverage with this embodiment is 0.95 to 1.65 microns with the 12.8 μm long linear array.

While spectrograph embodiments 1200, 1400, 1600, and 1800 have been designed for a Raman laser at wavelength of 1.03 or 1.064 microns, being all reflective optics except for the field lens, the same spectrographs can be utilized at any other Raman laser wavelength in the visible (400-700 nm) or near infrared (700-1100 nm). In certain embodiments, an ultraviolet (~200-400 nm) handheld Raman spectrograph can be designed using a fused silica field lens.

The imaging and linear array spectrograph embodiments discussed above are for a small handheld Raman spectrograph. Similar embodiments with much higher resolution can be designed for benchtop Raman systems or other systems that require limited wavelength coverage. The imaging and linear array spectrograph embodiments discussed above have superior resolution and throughput compared to traditional Czerny-Turner spectrographs.

The disclosure of each of U.S. Pat. No. 7,936,454 and U.S. Pat. No. 7,936,455 is incorporated herein by reference in its entirety to describe the laser induced breakdown spectroscopy (LIBS) implementations of the echelle spectrograph 100.

While the preferred embodiments of the present invention have been illustrated in detail, it should be apparent that modifications and adaptations to those embodiments may occur to one skilled in the art without departing from the scope of the present invention.

We claim:

1. A spectrograph that includes three mirrors and a field correcting lens in radiative communication with one another, the spectrograph comprising:
   a primary mirror having a concave reflective surface;
   a secondary mirror having a convex reflective surface and positioned to receive light reflected by the primary mirror;
   a tertiary mirror having a concave reflective surface and positioned to receive light reflected by the secondary mirror, wherein the primary mirror, the secondary mirror, and the tertiary mirror form a three-mirror anastigmat (TMA) with a substantially shared TMA parent vertex axis; and
   the field correcting lens having first and second surfaces and positioned to receive light from the tertiary mirror through the first surface and transmit said light through the second surface, wherein the TMA and the field correcting lens aggregately form a focusing optics unit of the spectrograph.

2. The spectrograph of claim 1, wherein the first surface of the field correcting lens is convex and the second surface of the field correcting lens is concave.

3. The spectrograph of claim 1, wherein the first surface of the field correcting lens is concave and the second surface of the field correcting lens is convex.

4. The spectrograph of claim 1, wherein the first surface of the field correcting lens is convex and the second surface of the field correcting lens is planar.

5. The spectrograph of claim 1, wherein the first surface of the field correcting lens is convex and the second surface of the field correcting lens is convex.

6. The spectrograph of claim 1, further comprising:
   an entrance aperture configured to receive light;
   an aperture stop;
   a collimator mirror configured to reflect said light in a collimated beam towards the aperture stop; and
   a diffraction grating configured to receive said light through the aperture stop and to disperse said light into multiple beams representing diffraction orders.

7. The spectrograph of claim 6, wherein the diffraction grating is an echelle diffraction grating.

8. The spectrograph of claim 6, further comprising:
   a prism, in optical communication with the diffraction grating, configured to receive and refract light that has passed through the entrance aperture into a plurality of beams dispersed according to wavelengths of said beams; and
   a fold mirror having a flat reflective surface and positioned to reflect light traversing through the prism to the focusing optics unit;
   wherein the entrance aperture, the collimator mirror, the diffraction grating, the prism, and the fold mirror form a light collimating and dispersing optics unit configured to collimate and disperse light that has passed through the entrance aperture.

9. The spectrograph of claim 8, wherein an optical axis of the collimating and dispersing optics unit passes through a middle of the aperture stop.

10. The spectrograph of claim 8, wherein:
    the prism is disposed between the diffraction grating and the fold mirror; and
    a light output from the prism comprises a plurality of spectral orders.

11. The spectrograph of claim 8, wherein the field correcting lens is a positive meniscus field correcting lens.

12. The spectrograph of claim 8, further comprising:
    a fiber optic cable input; and
    an optical sensor defining an image plane of the spectrograph,
    wherein the field correcting lens is disposed between the tertiary mirror and the optical sensor to receive the plurality of beams from the tertiary mirror and refract said plurality of beams onto the image plane;
    and wherein the first surface is a convex spherical surface and the second surface is a spherical concave surface.

13. The spectrograph of claim 8, wherein the field correcting lens is positioned such that the primary mirror, secondary mirror, tertiary mirror, and the field correcting lens substantially share the common TMA parent vertex axis.

14. The spectrograph of claim 8, further comprising a baffle enclosing a first straight light aperture therein, wherein the baffle is positioned such that light propagating from the primary mirror to the secondary mirror forms an intermediate focus in said first straight light aperture.

15. The spectrograph of claim 14, further comprising a second straight light aperture disposed between the tertiary mirror and the field correcting lens such that a plurality of the beams reflected from the tertiary mirror passes through the second straight light aperture and onto the first spherical and convex surface of the field correcting lens.

16. The spectrograph of claim 15, wherein the second straight light aperture does not obstruct with the beams passing from the secondary mirror to the tertiary mirror.

17. The spectrograph of claim 6, further comprising a diffraction order sorting filter.

18. The spectrograph of claim 17, wherein the optical axis of the collimating and dispersing optics unit of the spectrograph passes through the middle of the aperture stop.

19. The spectrograph of claim 17, wherein the field correcting lens is a positive meniscus field correcting lens.

20. The spectrograph of claim 17, further comprising:
a fiber optic cable input; and
an optical sensor defining an image plane of the spectrograph,
wherein the field correcting lens is disposed between the tertiary mirror and the optical sensor to receive a plurality of beams reflected from the tertiary mirror and refract said plurality of beams onto the image plane; and
wherein the first surface is a convex spherical surface and the second surface is a spherical concave surface.

21. The spectrograph of claim 17, wherein the field correcting lens is positioned such that the primary mirror, secondary mirror, tertiary mirror, and the field correcting lens substantially share the common TMA parent vertex axis.

22. The spectrograph of claim 17, further comprising a baffle enclosing a first straight light aperture therein, wherein the baffle is positioned such that light propagating from the primary mirror to the secondary mirror forms an intermediate focus in said first straight light aperture.

23. The spectrograph of claim 22, further comprising a second straight light aperture disposed between the tertiary mirror and the field correcting lens such that a plurality of the beams reflected from the tertiary mirror passes through the second straight light aperture and onto the first spherical and convex surface of the field correcting lens.

24. The spectrograph of claim 17, wherein the second straight light aperture does not obstruct with the beams passing from the secondary mirror to the tertiary mirror.

25. A spectrograph, comprising:
a diffraction grating;
a primary mirror having a concave reflective surface and positioned to reflect light that has interacted with the diffraction grating;
a secondary mirror having a convex reflective surface and positioned to receive said light from the primary mirror;
a tertiary mirror having a concave reflective surface and positioned to receive said light reflected by the secondary mirror, wherein the primary mirror, the secondary mirror, and the tertiary mirror form a three-mirror anastigmat (TMA) with a shared TMA parent vertex axis;
an entrance aperture;
an aperture stop; and
a collimator mirror positioned to receive light that has been transmitted through the entrance aperture and form a collimated beam of light directed towards the diffraction grating through the aperture stop.

26. The spectrograph of claim 25, wherein the diffraction grating is positioned to receive and diffract light that has passed through the aperture stop into a plurality of beams spatially dispersed by wavelength;
the diffraction grating is configured to be rotatable about a first axis that is perpendicular to the surface of a first plane of the grating such that a dispersion direction is caused to be perpendicular to a second plane, the second plane passing through the primary mirror, the secondary mirror, and the tertiary mirror of the TMA;
the diffraction grating configured to be rotatable about a second axis such that a rotation angle is substantially close to a blaze angle of the grating, wherein the second axis is parallel to a groove direction on the surface of the diffraction grating; and
the diffraction grating configured to be rotatable in the first plane of the grating about a third axis at an angle chosen to result in cancellation of the geometric distortion and causing said plurality of beams to intersect an image plane along a straight line in the center of the image plane, wherein the third axis is perpendicular to the groove.

27. The spectrograph of claim 25, wherein the diffraction grating is positioned to receive and diffract light that has passed through the aperture stop into a plurality of beams spatially dispersed by wavelength;
the diffraction grating is configured to be rotatable about a first axis that is perpendicular to the surface of a first plane of the grating such that a dispersion direction is caused to be parallel to a second plane, the second plane passing through the primary mirror, the secondary mirror, and the tertiary mirror of the TMA;
the diffraction grating configured to be rotatable about a second axis such that a rotation angle is substantially close to a blaze angle of the grating, wherein the second axis is parallel to a groove direction on the surface of the diffraction grating.

* * * * *